(12) United States Patent
Chan et al.

(10) Patent No.: US 11,439,660 B2
(45) Date of Patent: Sep. 13, 2022

(54) ANTIMICROBIAL POLY(ALKYLATED IMIDAZOLIUM) SALTS

(71) Applicants: NANYANG TECHNOLOGICAL UNIVERSITY, Singapore (SG); MASSACHUSETTS INSTITUTE OF TECHNOLOGY, Cambridge, MA (US)

(72) Inventors: Bee Eng Mary Chan, Singapore (SG); Paula T. Hammond, Cambridge, MA (US); Bo Liu, Singapore (SG); Wenbin Zhong, Singapore (SG)

(73) Assignees: Nanyang Technological University, Singapore (SG); Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 16/605,856

(22) PCT Filed: Apr. 18, 2018

(86) PCT No.: PCT/SG2018/050195
§ 371 (c)(1),
(2) Date: Oct. 17, 2019

(87) PCT Pub. No.: WO2018/194521
PCT Pub. Date: Oct. 25, 2018

(65) Prior Publication Data
US 2020/0046760 A1 Feb. 13, 2020

Related U.S. Application Data

(60) Provisional application No. 62/486,613, filed on Apr. 18, 2017.

(51) Int. Cl.
| | | |
|---|---|---|
| *A61K 31/787* | (2006.01) |
| *A61P 31/04* | (2006.01) |
| *A01N 43/50* | (2006.01) |
| *A61K 8/84* | (2006.01) |
| *A61Q 5/02* | (2006.01) |
| *A61Q 17/00* | (2006.01) |
| *A61Q 19/10* | (2006.01) |
| *C08G 73/06* | (2006.01) |
| *C11D 3/37* | (2006.01) |
| *C11D 3/48* | (2006.01) |
| *C11D 9/30* | (2006.01) |

(52) U.S. Cl.
CPC ........... *A61K 31/787* (2013.01); *A01N 43/50* (2013.01); *A61K 8/84* (2013.01); *A61P 31/04* (2018.01); *A61Q 5/02* (2013.01); *A61Q 17/005* (2013.01); *A61Q 19/10* (2013.01); *C08G 73/0616* (2013.01); *C11D 3/3723* (2013.01); *C11D 3/48* (2013.01); *C11D 9/30* (2013.01)

(58) Field of Classification Search
CPC .... A61K 31/787; C08G 73/0616; A61Q 5/02; A61Q 17/005; A61Q 19/10; C11D 3/3723; C11D 3/48; C11D 9/30
See application file for complete search history.

(56) References Cited

U.S. PATENT DOCUMENTS

| | | |
|---|---|---|
| 5,356,803 A | 10/1994 | Carpenter et al. |
| 6,689,372 B1 | 2/2004 | Hoelzl et al. |
| 7,169,745 B2 | 1/2007 | Kasturi et al. |
| 2011/0263810 A1 | 10/2011 | Siemer et al. |
| 2017/0215417 A1 | 8/2017 | Bhushan et al. |
| 2017/0247523 A1 | 8/2017 | Appavoo et al. |

FOREIGN PATENT DOCUMENTS

| | | |
|---|---|---|
| TW | 201040211 A1 | 11/2010 |
| WO | 2012127009 A1 | 9/2012 |
| WO | 2016020216 A1 | 2/2016 |
| WO | 2017025433 A1 | 2/2017 |

OTHER PUBLICATIONS

Berge et al. J. Pharm. Sci., 1977, 66 (1), 1-19.*
Hancock, Robert EW; et al. "Antimicrobial and host-defense peptides as new anti-infective therapeutic strategies." Nature biotechnology 24.12 (2006): 1551-1557.
Davis, Starkey D. "Activity of gentamicin, tobramycin, polymyxin B, and colistimethate in mouse protection tests with Pseudomonas aeruginosa." Antimicrobial agents and chemotherapy 8.1 (1975): 50-53.
Liu, Shaoqiong, et al. "Highly potent antimicrobial polyionenes with rapid killing kinetics, skin biocompatibility and in vivo bactericidal activity." Biomaterials 127 (2017): 36-48.
Zheng, Zhiqiang, et al. "Structure-antibacterial activity relationships of imidazolium-type ionic liquid monomers, poly (ionic liquids) and poly (ionic liquid) membranes: effect of alkyl chain length and cations." ACS applied materials & interfaces 8.20 (2016): 12684-12692.
Nederberg, Fredrik, et al. "Biodegradable nanostructures with selective lysis of microbial membranes." Nature chemistry 3.5 (2011): 409-414.

(Continued)

*Primary Examiner* — Alicia L Otton

(74) *Attorney, Agent, or Firm* — Thomas | Horstemeyer, LLP

(57) ABSTRACT

Disclosed herein are polymers containing repeating units of formula (I) or copolymers containing the repeating units of formula (I) and (II), where $R^1$ to $R^{12}$, m, n, p, q, x and y are as defined herein. The polymers and copolymers have an antimicrobial effect and may be used therapeutically or in formulations intended for use as detergents.

20 Claims, 15 Drawing Sheets

(56) References Cited

OTHER PUBLICATIONS

Yang, Chuan, et al. "Broad-Spectrum Antimicrobial Star Polycarbonates Functionalized with Mannose for Targeting Bacteria Residing inside Immune Cells." Advanced healthcare materials 5.11 (2016): 1272-1281.
Chin, Willy, et al. "Biodegradable broad-spectrum antimicrobial polycarbonates: investigating the role of chemical structure on activity and selectivity." Macromolecules 46.22 (2013): 8797-8807.
Lienkamp, Karen, et al. "Antimicrobial polymers prepared by ROMP with unprecedented selectivity: a molecular construction kit approach." Journal of the American Chemical Society 130.30 (2008): 9836-9843.
Al-Badri, Zoha M., et al. "Investigating the effect of increasing charge density on the hemolytic activity of synthetic antimicrobial polymers." Biomacromolecules 9.10 (2008): 2805-2810.
Hosseinnejad, Mahmoud; et al. "Evaluation of different factors affecting antimicrobial properties of chitosan." International journal of biological macromolecules 85 (2016): 467-475.
Li, Peng, et al. "Cationic peptidopolysaccharides show excellent broad-spectrum antimicrobial activities and high selectivity." Advanced Materials 24.30 (2012): 4130-4137.
Palermo, Edmund F.; et al. "Cationic spacer arm design strategy for control of antimicrobial activity and conformation of amphiphilic methacrylate random copolymers." Biomacromolecules 13.5 (2012): 1632-1641.
Kuroda, Kenichi; et al. "Amphiphilic polymethacrylate derivatives as antimicrobial agents." Journal of the American Chemical Society 127.12 (2005): 4128-4129.
Xiong, Menghua, et al. "Helical antimicrobial polypeptides with radial amphiphilicity." Proceedings of the National Academy of Sciences 112.43 (2015): 13155-13160.
Xi, Yuejing, et al. "Preparation and antibacterial mechanism insight of polypeptide-based micelles with excellent antibacterial activities." Biomacromolecules 17.12 (2016): 3922-3930.
Liu, Runhui, et al. "Tuning the biological activity profile of antibacterial polymers via subunit substitution pattern." Journal of the American Chemical Society 136.11 (2014): 4410-4418.
Mowery, Brendan P., et al. "Structure—activity relationships among random nylon-3 copolymers that mimic antibacterial host-defense peptides." Journal of the American Chemical Society 131.28 (2009): 9735-9745.
Chakraborty, Saswata, et al. "Ternary nylon-3 copolymers as host-defense peptide mimics: beyond hydrophobic and cationic subunits." Journal of the American Chemical Society 136.41 (2014): 14530-14535.

Langer, Robert. "New methods of drug delivery." Science 249.4976 (1990): 1527-1533.
Liu, Yuan, et al. "A biosurfactant-inspired heptapeptide with improved specificity to kill MRSA." Angewandte Chemie 129.6 (2017): 1508-1512.
Ling, Losee L., et al. "A new antibiotic kills pathogens without detectable resistance." Nature 517.7535 (2015): 455-459.
Lam, Shu J., et al. "Combating multidrug-resistant Gram-negative bacteria with structurally nanoengineered antimicrobial peptide polymers." Nature microbiology 1.11 (2016): 1-11.
Liu, Yi-Yun, et al. "Emergence of plasmid-mediated colistin resistance mechanism MCR-1 in animals and human beings in China: a microbiological and molecular biological study." The Lancet infectious diseases 16.2 (2016): 161-168.
Pethe, Kevin, et al. "A chemical genetic screen in *Mycobacterium tuberculosis* identifies carbon-source-dependent growth inhibitors devoid of in vivo efficacy." Nature communications 1.1 (2010): 1-8.
Ranke, Johannes, et al. "Biological effects of imidazolium ionic liquids with varying chain lengths in acute Vibrio fischeri and WST-1 cell viability assays." Ecotoxicology and environmental safety 58.3 (2004): 396-404.
Loh, B; et al. "Use of the fluorescent probe 1-N-phenylnaphthylamine to study the interactions of aminoglycoside antibiotics with the outer membrane of Pseudomonas aeruginosa." Antimicrobial agents and chemotherapy 26.4 (1984): 546-551.
Hancock, R. E., et al. "Interaction of aminoglycosides with the outer membranes and purified lipopolysaccharide and OmpF porin of *Escherichia coli*." Antimicrobial agents and chemotherapy 35.7 (1991): 1309-1314.
Vaara, Martti. "Agents that increase the permeability of the outer membrane." Microbiology and Molecular Biology Reviews 56.3 (1992): 395-411.
Zhang, Lijuan, et al. "Interactions of Bacterial Cationic Peptide Antibiotics with Outer and Cytoplasmic Membranes ofPseudomonas aeruginosa." Antimicrobial agents and chemotherapy 44.12 (2000): 3317-3321.
King, Allison, et al. "High antimicrobial effectiveness with low hemolytic and cytotoxic activity for PEG/quaternary copolyoxetanes." Biomacromolecules 15.2 (2014): 456-467.
Lindner "Imidazolium-Based Polymers via the Poly-Radziszewski Reaction", Macromolecules, Mar. 3, 2016, 49(6) 2046-2053 Abstract.
Grygiel et al. "Main-chain Polyimidazolium Polymers by One-Pot Synthesis and Application as Nitrogen-Doped Carbon Precursors", Macromolecular Chemistry and Physics, Mar. 21, 2017, 218(18)1-9.
Carlisle et al. "Main-chain imidazolium polymer membranes for CO2 separations: An initial study of a new ionic liquid-inspired platform", Journal of Membrance Science, Oct. 22, 2009, 359(1-2)37-43.

* cited by examiner (e)

(f)

ANTIMICROBIAL POLY(ALKYLATED IMIDAZOLIUM) SALTS

FIELD OF INVENTION

This invention relates to poly(alkylated imidazolium) chloride salts and their use as antimicrobial agents towards a wide spectrum of bacteria, as well as compositions containing said polymeric salts.

BACKGROUND

The listing or discussion of a prior-published document in this specification should not necessarily be taken as an acknowledgement that the document is part of the state of the art or is common general knowledge.

The emergence and spread of difficult-to-treat multidrug resistant pathogens is a matter of great concern to the world's healthcare systems, research communities, clinicians, government agencies and general population at large. Recently, the World Health Organization (WHO) has released a list of bacteria for which new antibiotics or antibacterial agents are urgently needed. The list was drawn up in a bid to guide and promote research and development of new antibiotics as part of the WHO's efforts to address growing global resistance to antimicrobial medicines. The top most critical bacteria in the list are carbapenem-resistant *Acinetobacter baumannii* (CRAB), carbapenem-resistant *Pseudomonas aeruginosa* (CRPA) and extended-spectrum beta-lactamases (ESBL)-producing carbapenem-resistant Enterobacteriaceae (CREB). Some examples of ESBL-CREB include carbapenem-resistant *Escherichia coli, Enterobacter aerogenes, Enterobacter cloacae* complex, *Klebsiella pneumoniae* and *Klebsiella oxytoca*.

An alternative class of antibacterial drugs are antimicrobial peptides (AMPs) which are regarded as promising candidates for treating multidrug-resistant bacteria. However, their current use is often limited by high toxicity towards mammalian cells and/or generally higher minimum inhibitory concentrations (e.g. see Hancock, R. E. et al., *Nat. Biotechnol.*, 2006. 24, 1551-1557). Examples of AMPs include the polymyxins, which are a group of cyclic lipopeptides that generally show antimicrobial selectivity towards Gram-negative bacteria. However, the polymyxins have specific amino acid sequences that make them generally expensive to produce (Davis, S. D., *Antimicrob. Agents Chemother.*, 1975, 8, 50-53). In addition, the use of colistin (polymyxin E) can result in negative side effects like nephrotoxicity and so it has been considered to be used only as a last-resort if other antibiotics failed.

Besides peptides, synthetic polymers have also been widely applied as disinfectants due to potent antibacterial effect, though they generally exhibit higher toxicity towards mammalian cells. Some examples of widely used antibacterial polymers are polyhexamethylene biguanide (PHMB) and quaternary ammonium polymers such as poly(diallyldimethylammonium chloride) (PDADMAC). Other promising antimicrobial polymers that have been reported include:

quaternary ammonium polymers (Liu, S., et al., *Biomaterials*, 2017, 127, 36-48; King, A., et al., *Biomacromolecules*, 2014, 15, 456-467);

polyimidazolium polymers (Zheng, Z., et al., *ACS Appl. Mater. Interfaces*, 2016, 8, 12684-12692);

polycarbonates (Nederberg, F., et al., *Nat. Chem.*, 2011, 3, 409-414; Yang, C., et al., *Adv. Healthcare Mater.*, 2016, 5, 1272-1281; Chin, W., et al., *Macromolecules*, 2013, 46, 8797-8807);

polynorbornene (Lienkamp, K., et al., *J. Am. Chem. Soc.*, 2008, 130, 9836-9843; Al-Badri, Z. M., et al., *Biomacromolecules*, 2008, 9, 2805-2810);

chitosan derivatives (Hosseinnejad, M. et al., *Int. J. Biol. Macromol.*, 2016, 85, 467-475; Li, P., et al., *Adv. Mater.*, 2012, 24, 4130-4137);

polymethacrylamides (Palermo, E. F., et al., *Biomacromolecules*, 2012. 13, 1632-1641; Kuroda, K. et al., *J. Am. Chem. Soc.*, 2005, 127, 4128-4129);

other polypeptides (Xiong, M., et al., *Proc. Natl. Acad. Sci. U.S.A.*, 2015. 112, 13155-13160; Xi, Y., et al., *Biomacromolecules*, 2016, 17, 3922-3930); and poly(beta-peptides) (Liu, R., et al., *J. Am. Chem. Soc.*, 2014, 136, 4410-4418; Mowery, B. P., et al., *J. Am. Chem. Soc.*, 2009, 131, 9735-9745; Chakraborty, S., et al., *J. Am. Chem. Soc.*, 2014. 136, 14530-14535).

Most of these polymers are synthesised via free radical polymerisation (FRP) or ring opening polymerisation (ROP), which may then be followed by post-functionalisation. The synthetic routes typically involve large quantities of organic solvents and produce highly toxic products. In addition, the syntheses are difficult to scale up, which makes such polymers unable to be synthesised in large quantity.

Given the above, there remains a need for new antimicrobial agents that demonstrate high antimicrobial activity towards a broad spectrum of microorganisms, and at the same time exhibit low toxicity towards mammalian cells and are easy and cheap to produce in large quantity. Such antimicrobial agents can potentially be used as pharmaceutical products for bacterial infections, or can be advantageously incorporated into cleaning agents (such as soaps, detergents and shampoo), personal care and hygiene products.

SUMMARY OF INVENTION

The invention is described below with regard to the following numbered aspects and embodiments.

1. A polymer having a repeating unit of formula (I):

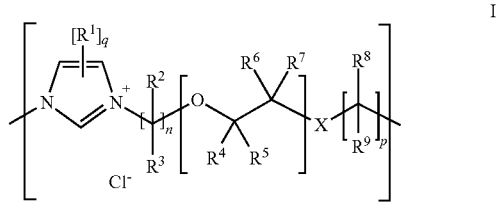

or a copolymer comprising the repeating unit of formula I and a repeating unit of formula (II):

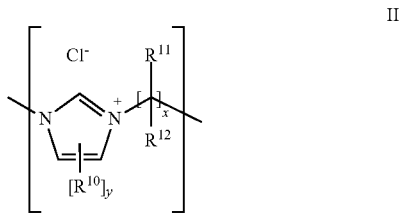

wherein:

$R^1$ and $R^{10}$, when present, independently represent $C_{1-6}$ alkyl;

each $R^2$ to $R^8$ and $R^{11}$ independently represent H or $C_{1-6}$ alkyl;

each $R^9$ and $R^{12}$ independently represents $CO_2R^{13}$ or, more particularly, H or $C_{1-6}$ alkyl;

$R^{13}$ represents H or $C_{1-6}$ alkyl;

X represents $CR^{14}R^{15}$, O or S;

$R^{14}$ and $R^{15}$ independently represent $CO_2R^{13}$ or, more particularly, H or $C_{1-6}$ alkyl;

m is a number selected from 0 to 5;
n is a number selected from 2 to 10;
p is a number selected from 0 to 5;
q is a number selected from 0 to 3;
x is a number selected from 2 to 10;
y is a number selected from 0 to 3; and
solvates thereof,
provided that, when the compound is a copolymer, the repeating unit of formula (I) and the repeating unit of formula (II) are not the same.

2. The polymer or copolymer according to Clause 1, wherein:

$R^1$ and $R^{10}$, when present, independently represent $C_{1-3}$ alkyl;

each $R^2$ to $R^8$ and $R^{11}$ independently represents H or methyl;

each $R^9$ and $R^{12}$ independently represents $CO_2R^{13}$ or, more particularly, H or $C_{1-3}$ alkyl;

$R^{13}$ represents H or $C_{1-3}$ alkyl;

X represents $CR^{14}R^{15}$ or O;

$R^{14}$ and $R^{15}$ independently represent $CO_2R^{13}$ or, more particularly, H or $C_{1-3}$ alkyl;

m is a number selected from 0 to 4;
n is a number selected from 2 to 8;
p is a number selected from 0 to 3;
q is a number selected from 0 to 1;
x is a number selected from 2 to 8; and
y is a number selected from 0 to 1.

3. The polymer or copolymer according to Clause 1 or Clause 2, wherein:

each $R^2$ to $R^8$ and $R^{11}$ independently represents H;

each $R^9$ and $R^{12}$ independently represents $CO_2H$ or, more particularly, H or methyl;

X represents $CR^{14}R^{15}$ or O;

$R^{14}$ and $R^{15}$ independently represent $CO_2H$ or, more particularly, H or methyl;

m is a number selected from 0 to 3;
n is a number selected from 2 to 7;
p is a number selected from 0 to 2;
q and y are 0; and
x is a number selected from 2 to 7.

4. The polymer or copolymer according to any one of the preceding clauses, wherein:

each $R^2$ to $R^8$ and $R^{11}$ independently represents H;

each $R^9$ and $R^{12}$ independently represents $CO_2H$ or, more particularly, H or methyl;

X represents $CR^{14}R^{15}$ or O;

$R^{14}$ and $R^{15}$ independently represent $CO_2H$ or, more particularly, H or methyl;

m is a number selected from 0 to 2;
n is a number selected from 2 to 7;
p is a number selected from 0 to 2;
q and y are 0; and
x is a number selected from 2 to 7.

5. The polymer or copolymer according to any one of the preceding clauses, wherein the number average molecular weight is from 500 to 7,000 Daltons.

6. The polymer or copolymer according to any one of the preceding clauses, wherein the polymer or copolymer is a polymer having the repeating unit of formula I.

7. The polymer of Clause 6, wherein:

each of $R^2$ to $R^8$ are H;

each $R^9$ represents $CO_2H$ or, more particularly, H or methyl;

X represents $CH_2$ or O;

m is a number selected from 0 to 2;
n is a number selected from 2 to 6;
p is a number selected from 0 to 2;
q is 0.

8. The polymer or copolymer according to any one of the preceding clauses, wherein when X is O, p is 1 or 2.

9. The polymer according to any one of Clauses 1 to 8, wherein the repeating unit is selected from the group consisting of:

(i)

optionally wherein the number average molecular weight of the polymer is from 500 to 2,500 Daltons;

(ii)

optionally wherein the number average molecular weight of the polymer is from 500 to 2,500 Daltons;

(iii)

optionally wherein the number average molecular weight of the polymer is from 500 to 2,500 Daltons;

(iv)

optionally wherein the number average molecular weight of the polymer is from 500 to 2,000 Daltons;

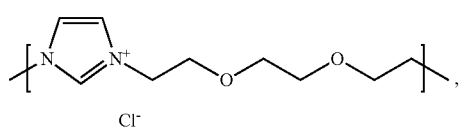
(v)

optionally wherein the number average molecular weight of the polymer is from 4,000 to 5,500 Daltons;

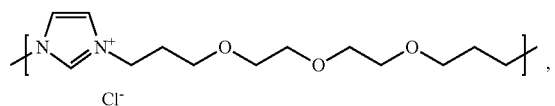
(vi)

optionally wherein the number average molecular weight of the polymer is from 4,000 to 5,000 Daltons; and

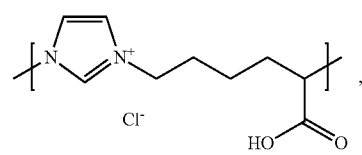
(vii)

optionally wherein the number average molecular weight of the polymer is from 500 to 2,000 Daltons.

10. The polymer according to Clause 9, wherein the repeating unit is selected from the group consisting of:

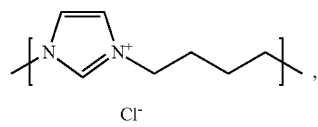
(i)

wherein the number average molecular weight of the polymer is from 500 to 2,000 Daltons;

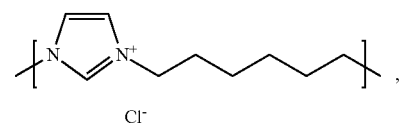
(ii)

wherein the number average molecular weight of the polymer is from 500 to 2,000 Daltons;

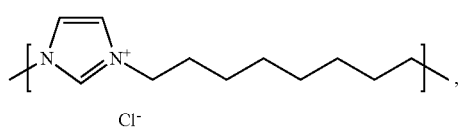
(iii)

wherein the number average molecular weight of the polymer is from 500 to 2,000 Daltons;

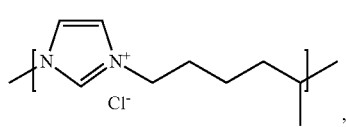
(iv)

wherein the number average molecular weight of the polymer is from 500 to 2,000 Daltons;

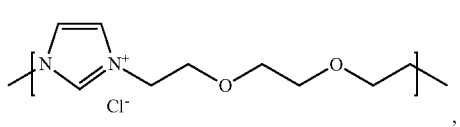
(v)

wherein the number average molecular weight of the polymer is from 4,000 to 5,500 Daltons; and

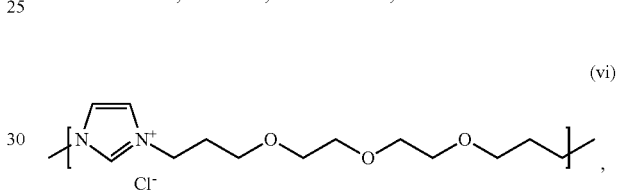
(vi)

wherein the number average molecular weight of the polymer is from 4,000 to 5,000 Daltons.

11. The copolymer according to any one of Clauses 1 to 5, wherein the repeating unit of formula (I) and formula (II) are selected from the group consisting of:

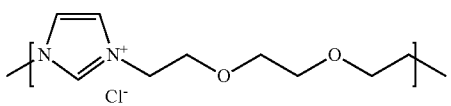
(i)

as the repeating unit of formula (I) and

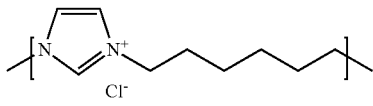
(ii)

as the repeating unit of formula (II), optionally wherein the number average molecular weight of the copolymer is from 1,000 to 5,000 Daltons; and

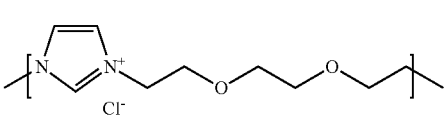
(ii)

as the repeating unit of formula (I) and

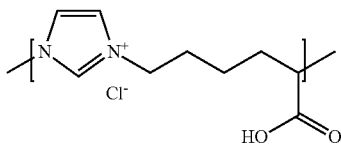

as the repeating unit of formula (II), optionally wherein the number average molecular weight of the copolymer is from 1,000 to 5,000 Daltons.

12. A pharmaceutical composition comprising the polymer or copolymer of any one of Clauses 1 to 11 and a pharmaceutically acceptable carrier.

13. A polymer or copolymer of any one of Clauses 1 to 11, or a pharmaceutical composition as described in Clause 12, for use as a medicament.

14. A method of treating a subject suffering from a microbial and/or fungal infection comprising the steps of administering to the subject a therapeutically effective amount of the polymer or copolymer of any one of Clauses 1 to 11, or a pharmaceutical composition as described in Clause 12, such that the infection is treated.

15. Use of a polymer or copolymer of any one of Clauses 1 to 11, or a pharmaceutical composition as described in Clause 12, in the manufacture of a medicament to treat a microbial and/or fungal infection in a subject in need thereof.

16. A polymer or copolymer of any one of Clauses 1 to 11, or a pharmaceutical composition as described in Clause 12, for use in the treatment of a microbial and/or fungal infection.

17. An antimicrobial and/or antifungal detergent composition comprising:
a polymer or copolymer as described in any one of Clauses 1 to 11; and
a surfactant.

18. The antimicrobial and/or antifungal detergent composition according to Clause 17, wherein the composition is in the form of a solid or liquid soap.

19. The antimicrobial and/or antifungal detergent composition according to Clause 17, wherein the composition is in the form of a shampoo.

DESCRIPTION

Figure 1:
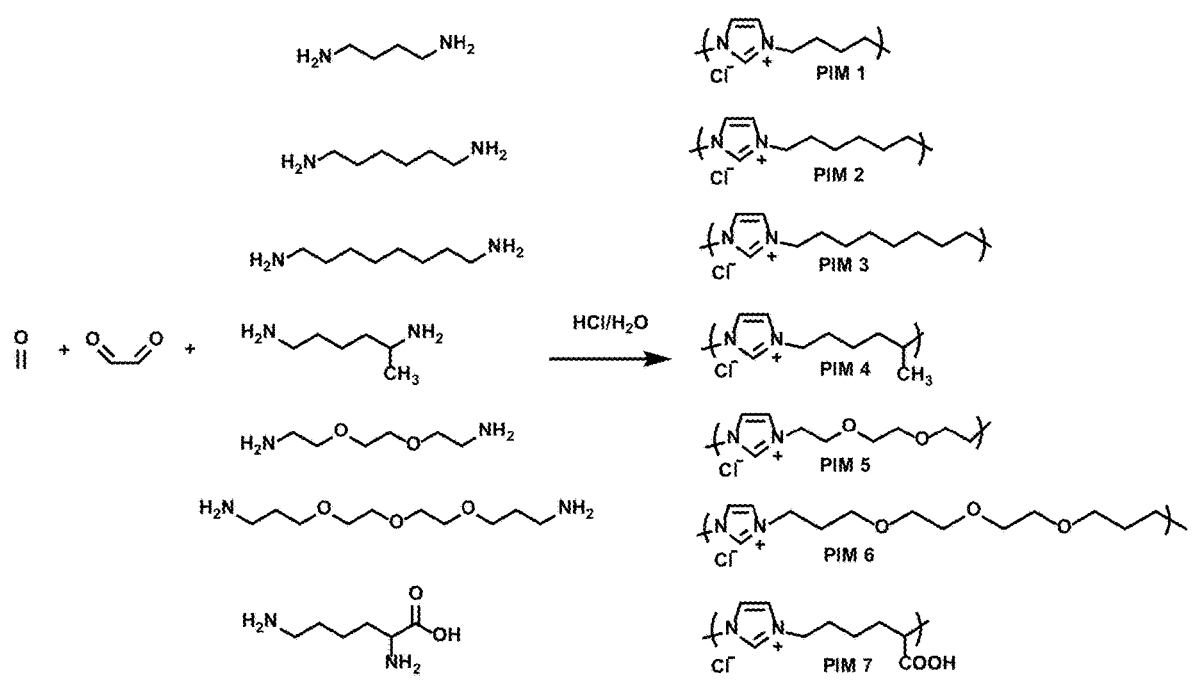
FIG. 1 Depicts the synthesis of PIM 1-7 chlorides from hydrochloric acid, diamines, formaldehyde and glyoxal via the Debus-Radziszewski reaction.
Figure 2:
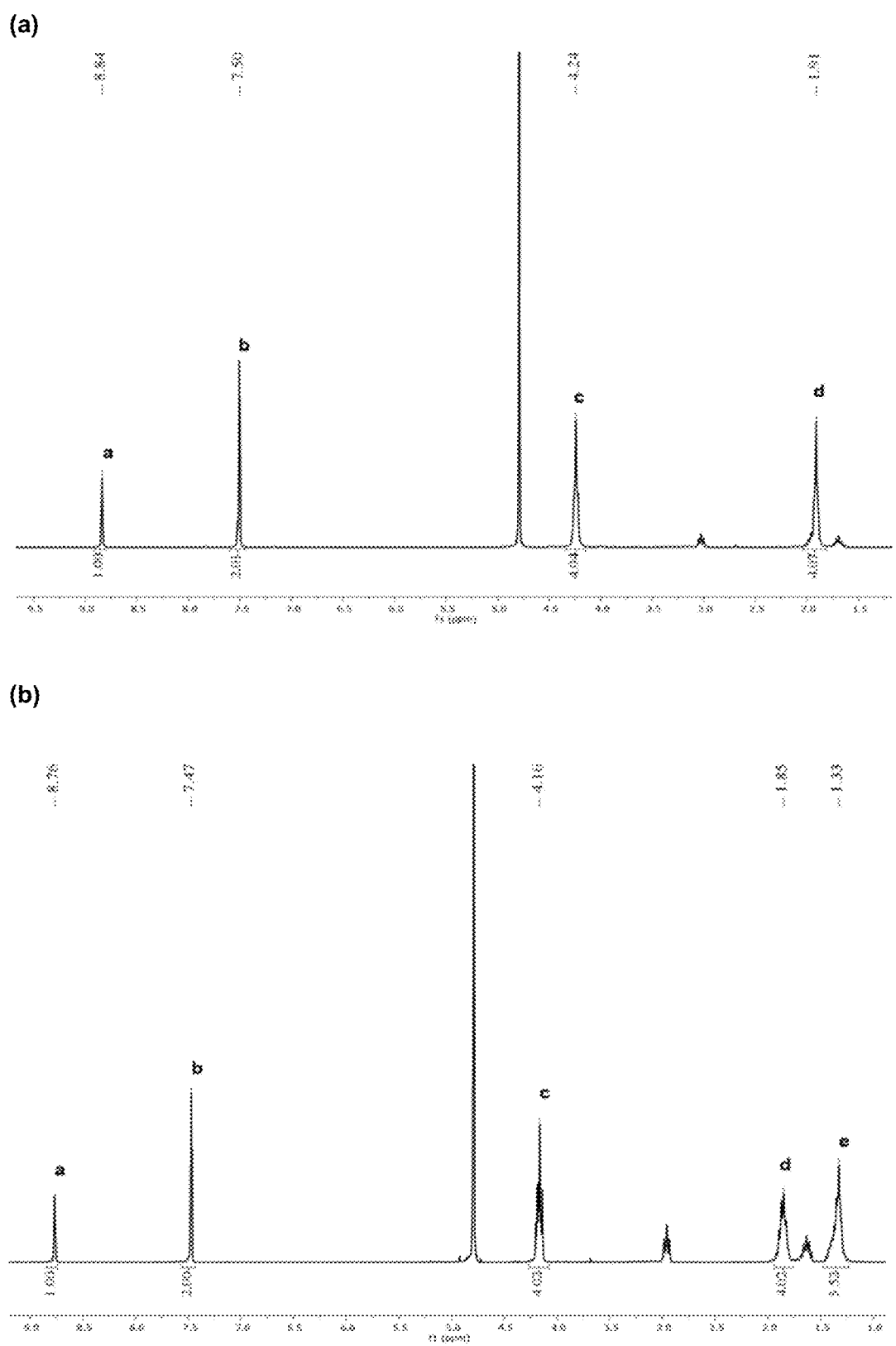
FIG. 2 Depicts the $^1$H NMR spectra (in $D_2O$) of (a) PIM 1; (b) PIM 2; (c) PIM 3; (d) PIM 4; (e) PIM 5; (f) PIM 6; and (g) PIM 7.
Figure 2:
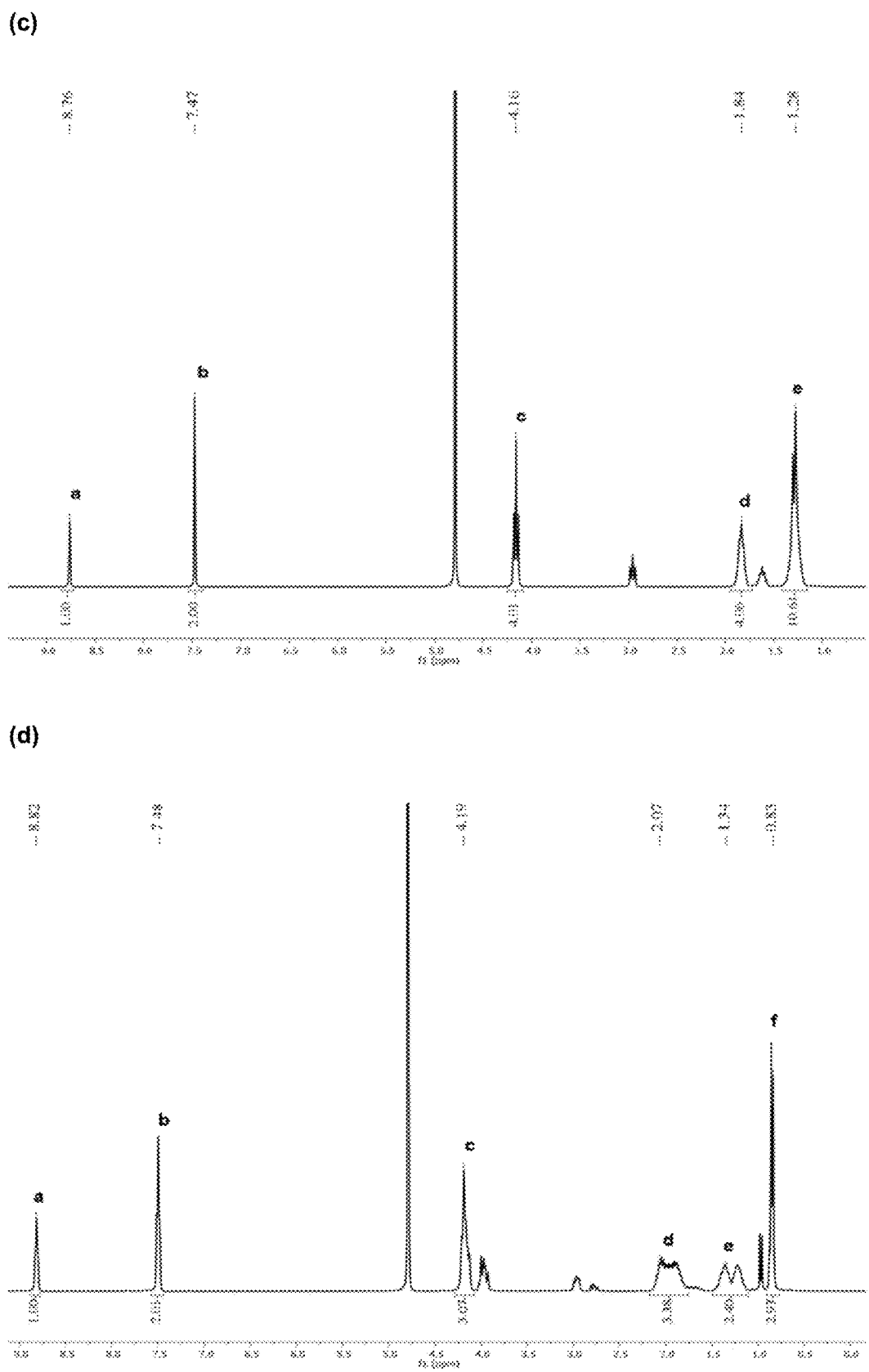
Figure 2:
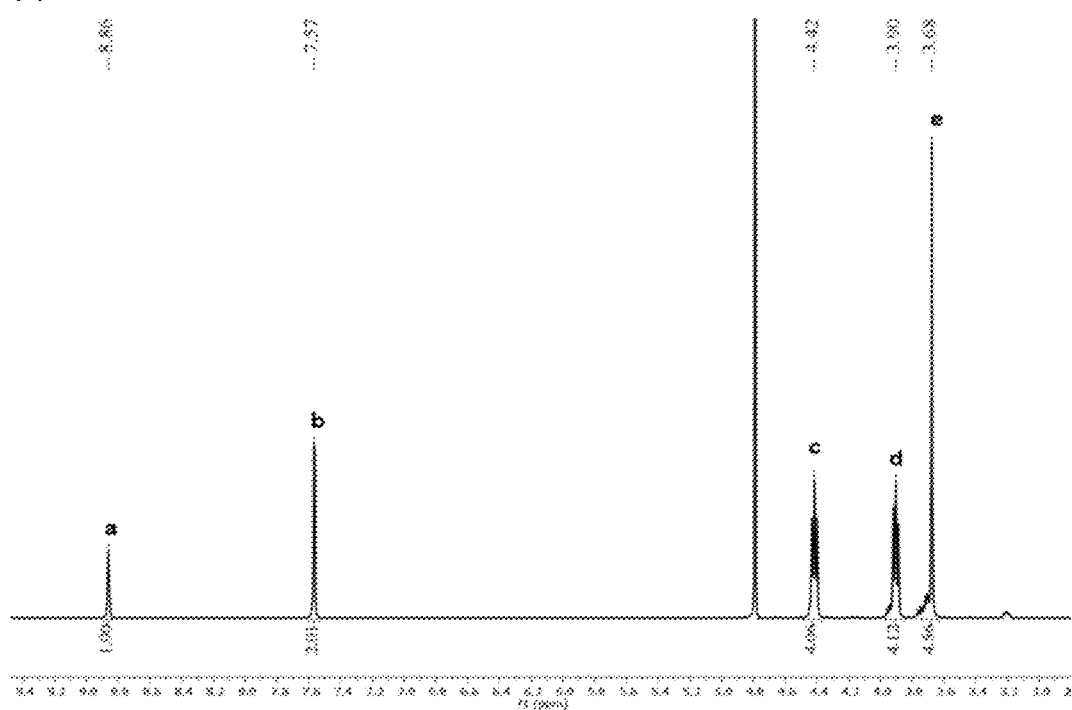
Figure 2:
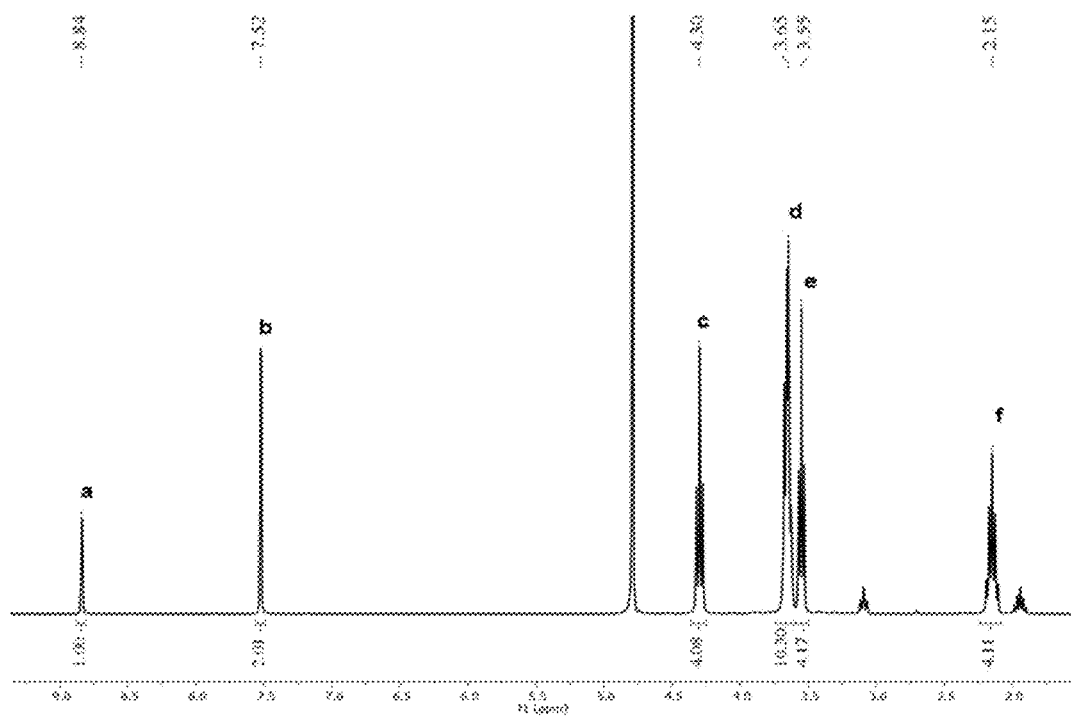
Figure 2:
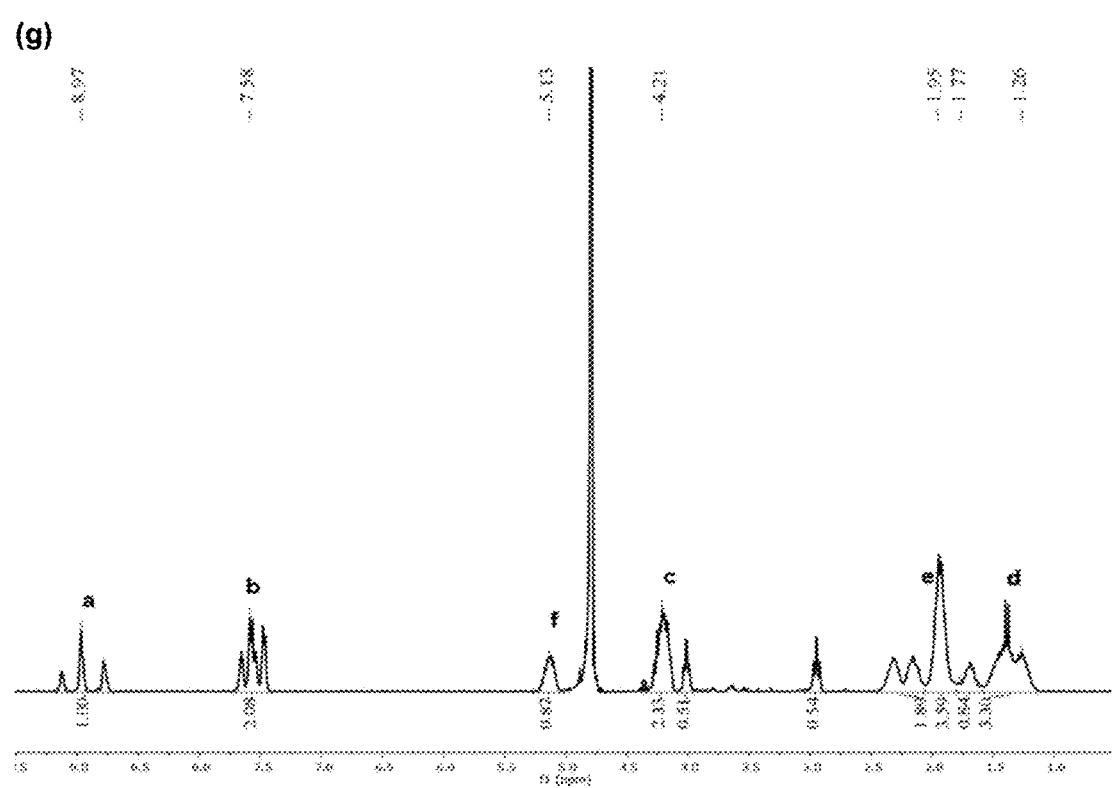
Figure 3:
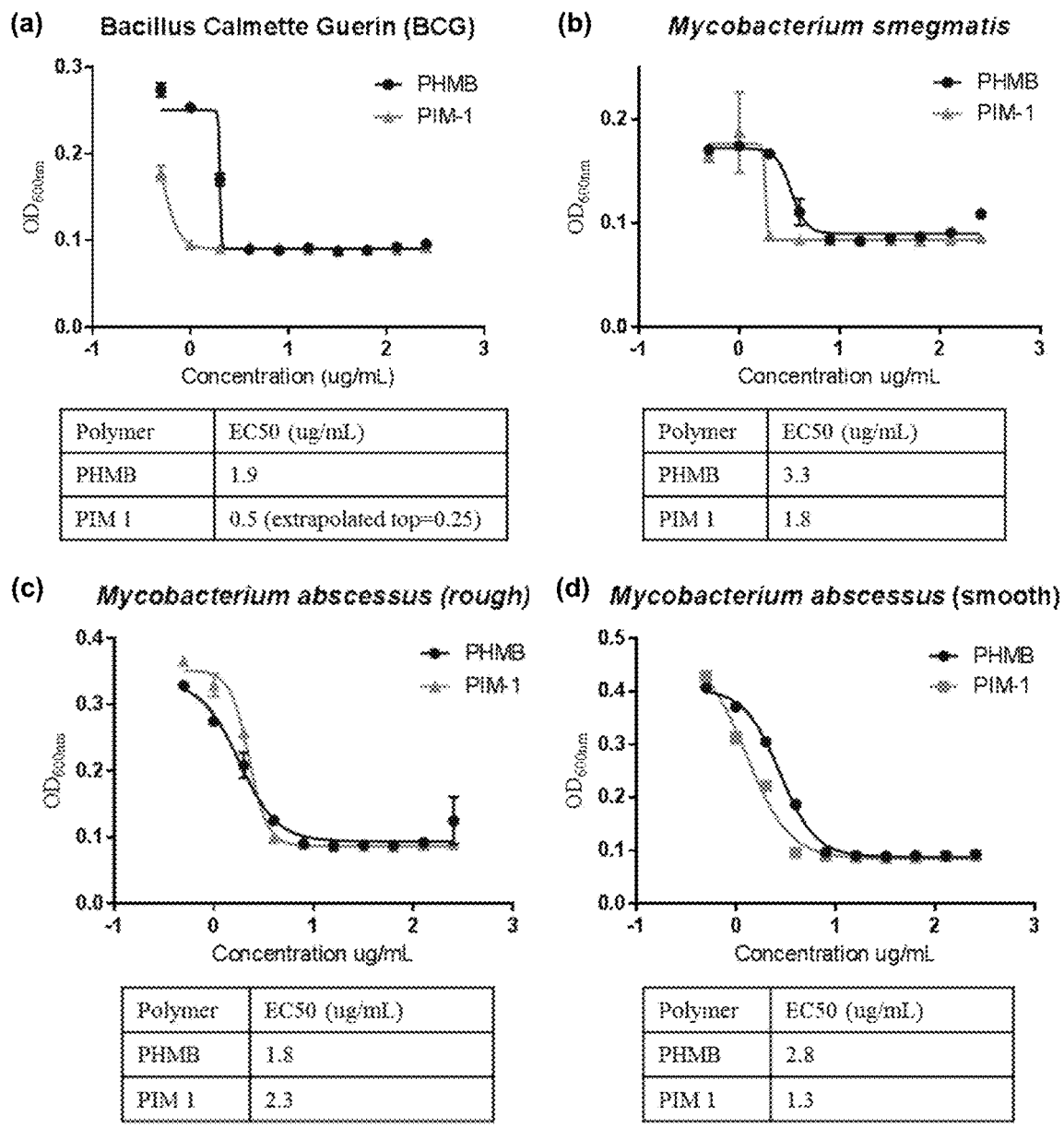
FIG. 3 Depicts the dose-response curves of PIM 1 chloride and polyhexamethylene biguanide (PHMB) on various mycobacterium: (a) Bacillus Calmette Guerin (BCG); (b) *Mycobacterium smegmatis*; (c) *Mycobacterium abscessus* (rough morphotype); and (d) *Mycobacterium abscessus* (smooth morphotype).

Disclosed herein are a series of cationic polymers, the cationic poly(alkylated imidazolium) (PIM) chloride salts, with the charge constrained to the main chain and aliphatic backbones with different degrees of hydrophobicity. These PIMs were synthesized from simple and inexpensive starting chemicals (formaldehyde, glyoxal, acid and water) using a one-step Debus-Radziszewski (DR) reaction. Surprisingly, these PIM chloride salts exhibit excellent broad-spectrum antimicrobial properties against a range of clinically important ESKAPE (*Enterococcus faecium, Staphylococcus aureus, Klebsiella pneumoniae, Acinetobacter baumannii, Pseudomonas aeruginosa,* and *Enterobacter*) bacteria species. Regardless of the details of their structure, the tested PIMs exhibit low hemolysis and the ones which have good antimicrobial efficacy have very high selectivity for these pathogens over human red blood cells (with selectivity >5000~10 000), i.e. low toxicity to mammalian cells. In contrast, the acetate salts of the same PIM molecules exhibit significantly higher toxicity to mammalian cells. In addition, the polymers disclosed herein have been found to be active against both Gram-positive and Gram-negative bacteria.

The term "Gram-positive bacteria" refers to bacteria having cell walls with high amounts of peptidoglycan. Gram-positive bacteria are identified by their tendency to retain crystal violet and stain dark blue or violet in the Gram staining protocol.

The term "Gram-negative bacteria" refers to bacteria having thinner peptidoglycan layers which do not retain the crystal violet stain in the Gram staining protocol and instead retain the counterstain, typically safranin. Gram-negative bacteria stain red or pink in the Gram staining protocol.

Thus, according to the first aspect of the invention, there is provided a polymer having a repeating unit of formula (I):

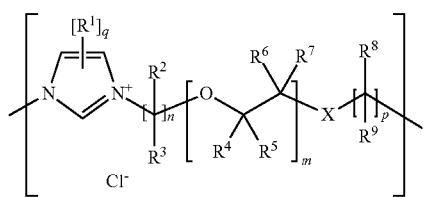

or a copolymer comprising the repeating unit of formula I and a repeating unit of formula (II):

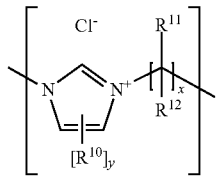

wherein:
$R^1$ and $R^{10}$, when present, independently represent $C_{1-6}$ alkyl;
each $R^2$ to $R^8$ and $R^{11}$ independently represent H or $C_{1-6}$ alkyl;
each $R^9$ and $R^{12}$ independently represents $CO_2R^{13}$ or, more particularly, H or $C_{1-6}$ alkyl;
$R^{13}$ represents H or $C_{1-6}$ alkyl;
X represents $CR^{14}R^{15}$, O or S;
$R^{14}$ and $R^{15}$ independently represent $CO_2R^{13}$ or, more particularly, H or $C_{1-6}$ alkyl;
m is a number selected from 0 to 5;
n is a number selected from 2 to 10;
p is a number selected from 0 to 5;
q is a number selected from 0 to 3;
x is a number selected from 2 to 10;
y is a number selected from 0 to 3; and
solvates thereof,
provided that, when the compound is a copolymer, the repeating unit of formula (I) and the repeating unit of formula (II) are not the same.
References herein (in any aspect or embodiment of the invention) to polymers or copolymers of the invention includes references to such compounds per se, to tautomers of such compounds, as well as to pharmaceutically acceptable solvates of such compounds.

As mentioned above, also encompassed by polymers or copolymers of the invention are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallizing the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGA), differential scanning calorimetry (DSC) and X-ray crystallography.

The solvates can be stoichiometric or non-stoichiometric solvates. Particularly preferred solvates are hydrates, and examples of hydrates include hemihydrates, monohydrates and dihydrates.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

The polymers or copolymers of the invention may exist as regioisomers and may also exhibit tautomerism. All tautomeric forms and mixtures thereof are included within the scope of the invention.

The polymers or copolymers of the invention may contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

The polymers or copolymers of the invention in the above-mentioned aspect of the invention may be utilised in a method of medical treatment. Thus, according to further aspects of the invention, there is provided:
(a) a polymer or copolymer of the invention for use in medicine;
(b) a polymer or copolymer of the invention for use in the treatment of a microbial and/or fungal infection;
(c) use of a polymer or copolymer of the invention for the preparation of a medicament for the treatment of a microbial and/or fungal infection; and (d) a method of treatment of a microbial and/or fungal infection, which method comprises the administration of an effective amount of a polymer or copolymer of the invention.

In embodiments that may be mentioned herein, the polymer or copolymer of the invention may be particularly useful with regard to microbial infections.

The term "microbial infection" covers any disease or condition caused by a microbial organism in or on a subject. Examples of microbial infections include, but are not limited to, tuberculosis caused by mycobacteria, burn wound infections caused by *pseudomonas* etc., skin infections caused by *S. aureus*, wound infections caused by *pseudomonas* and *A. baumannii*, and Sepsis. The term "fungal infection" covers any disease or condition caused by a microbial organism in or on a subject. Examples of microbial infections include, but are not limited to, athlete's foot, ringworm, yeast infections, and jock itch.

A non-limiting list of bacteria that may be susceptible to the polymers and copolymers of the invention include: *Acidothermus cellulyticus, Actinomyces odontolyticus, Alkaliphilus metalliredigens, Alkaliphilus oremlandii, Arthrobacter aurescens, Bacillus amyloliquefaciens, Bacillus clausii, Bacillus halodurans, Bacillus licheniformis, Bacillus pumilus, Bacillus subtilis, Bifidobacterium adolescentis, Bifidiobacterium longum, Caldicellulosiruptor saccharolyticus, Carboxydothermus hydrogenoformans, Clostridium acetobutylicum, Clostridium beijerinckii, Clostridium botulinum, Clostridium cellulolyticum, Clostridium difficile, Clostridium kluyveri, Clostridium leptum, Clostridium novyi, Clostridium perfringens, Clostridium tetani, Clostridium thermocellum, Corynebacterium diphtheriae, Corynebacterium efficiens, Corynebacterium glutamicum, Corynebacterium jeikeium, Corynebacterium urealyticum, Desulfitobacterium hafniense, Desulfotomaculum reducens, Eubacterium ventriosum, Exiguobacterium sibiricum, Fingoldia magna, Geobacillus kaustophilus, Geobacillus thermodenitrificans, Janibacter sp., Kineococcus radiotolerans, Lactobacillus fermentum, Listeria monocytogenes, Listeria innocua, Listeria welshimeri, Moorella thermoacetica, Mycobacterium avium, Mycobacterium bovis, Mycobacterium gilvum, Mycobacterium leprae, Mycobacterium paratuberculosis, Mycobacterium smegmatis, Mycobacterium tuberculosis, Mycobacterium ulcerans, Mycobacterium vanbaalenii, Nocardioides sp., Nocardia farcinica, Oceanobacillus iheyensis, Pelotomaculum thermopropionicum, Rhodococcus sp., Saccharopolyspora erythraea,* coagulase-negative *Staphylococcus* species, *Staphylococcus aureus*, methicillin resistant *Staphylococcus aureus* (MRSA), *Staphylococcus epidermidis*, methicillin resistant *Staphylococcus epidermidis* (MRSE), *Streptococcus agalactiae, Streptococcus gordonii, Streptococcus mitis, Streptococcus oralis, Streptococcus pneumoniae, Streptococcus sanguinis, Streptococcus suis, Streptomyces avermitilis, Streptomyces coelicolor, Thermoanaerobacter ethanolicus, Thermoanaerobacter tengcongensis*, and combinations thereof.

For the avoidance of doubt, in the context of the present invention, the term "treatment" includes references to therapeutic or palliative treatment of patients in need of such treatment, as well as to the prophylactic treatment and/or diagnosis of patients which are susceptible to the relevant disease states.

The terms "patient" and "patients" include references to mammalian (e.g. human) patients. As used herein the terms "subject" or "patient" are well-recognized in the art, and, are used interchangeably herein to refer to a mammal, including dog, cat, rat, mouse, monkey, cow, horse, goat, sheep, pig, camel, and, most preferably, a human. In some embodiments, the subject is a subject in need of treatment or a subject with a disease or disorder. However, in other embodiments, the subject can be a normal subject. The term does not denote a particular age or sex. Thus, adult and newborn subjects, whether male or female, are intended to be covered.

The term "effective amount" refers to an amount of a compound, which confers a therapeutic effect on the treated patient (e.g. sufficient to treat or prevent the disease). The effect may be objective (i.e. measurable by some test or marker) or subjective (i.e. the subject gives an indication of or feels an effect).

Unless otherwise stated, the term "alkyl" refers to an unbranched or branched saturated hydrocarbyl radical, which may be substituted or unsubstituted. Where the term "alkyl" refers to a $C_{1-6}$ alkyl (the alkyl group may be ethyl, propyl, (e.g. n-propyl or isopropyl), butyl (e.g. branched or unbranched butyl), pentyl or, more preferably, methyl).

For the avoidance of doubt, in cases in which the identity of two or more substituents in a polymer or copolymer of the invention may be the same, the actual identities of the respective substituents are not in any way interdependent.

Embodiments of the invention that may be mentioned include those that relate to polymers or copolymers of the invention in which:

$R^1$ and $R^{10}$, when present, independently represent $C_{1-3}$ alkyl;

each $R^2$ to $R^8$ and $R^{11}$ independently represents H or methyl;

each $R^9$ and $R^{12}$ independently represents $CO_2R^{13}$ or, more particularly, H or $C_{1-3}$ alkyl;

$R^{13}$ represents H or $C_{1-3}$ alkyl;

X represents $CR^{14}R^{15}$ or O;

$R^{14}$ and $R^{15}$ independently represent $CO_2R^{13}$ or, more particularly, H or $C_{1-3}$ alkyl;

m is a number selected from 0 to 4;
n is a number selected from 2 to 8;
p is a number selected from 0 to 3;
q is a number selected from 0 to 1;
x is a number selected from 2 to 8; and
y is a number selected from 0 to 1.

In further embodiments of the invention that may be mentioned include those that relate to polymers or copolymers of the invention in which:

$R^1$ and $R^{10}$, when present, independently represent $C_{1-6}$ alkyl (e.g. $R^1$ and $R^{10}$, when present, independently represent $C_{1-3}$ alkyl);

each $R^2$ to $R^8$ and $R^{11}$ independently represents H;

each $R^9$ and $R^{12}$ independently represents $CO_2H$ or, more particularly, H or methyl;

X represents $CR^{14}R^{15}$ or O;

$R^{14}$ and $R^{15}$ independently represent $CO_2H$ or, more particularly, H or methyl;

m is a number selected from 0 to 3;
n is a number selected from 2 to 7;
p is a number selected from 0 to 2;
q and y are 0; and
x is a number selected from 2 to 7.

In yet further embodiments of the invention that may be mentioned include those that relate to polymers or copolymers of the invention in which:

$R^1$ and $R^{10}$, when present, independently represent $C_{1-6}$ alkyl (e.g. $R^1$ and $R^{10}$, when present, independently represent $C_{1-3}$ alkyl);

each $R^2$ to $R^8$ and $R^{11}$ independently represents H;
each $R^9$ and $R^{12}$ independently represents $CO_2H$ or, more particularly, H or methyl;
X represents $CR^{14}R^{15}$ or O;
$R^{14}$ and $R^{15}$ independently represent $CO_2H$ or, more particularly, H or methyl;
m is a number selected from 0 to 3;
n is a number selected from 2 to 7;
p is a number selected from 0 to 2;
q and y are 0; and
x is a number selected from 2 to 7.

In yet still further embodiments of the invention that may be mentioned include those that relate to polymers or copolymers of the invention in which:
$R^1$ and $R^{10}$, when present, independently represent $C_{1-6}$ alkyl (e.g. $R^1$ and $R^{10}$, when present, independently represent $C_{1-3}$ alkyl);
each $R^2$ to $R^8$ and $R^{11}$ independently represents H;
each $R^9$ and $R^{12}$ independently represents $CO_2H$ or, more particularly, H or methyl;
X represents $CR^{14}R^{15}$ or O;
$R^{14}$ and $R^{15}$ independently represent $CO_2H$ or, more particularly, H or methyl;
m is a number selected from 0 to 2;
n is a number selected from 2 to 7;
p is a number selected from 0 to 2;
q and y are 0; and
x is a number selected from 2 to 7.

The polymers and copolymers of the invention may have any suitable number average molecular weight. For example, the polymers and copolymers of the invention may have a number average molecular weight of from 500 to 7,000 Daltons, such as from 500 to 5,500 Daltons, such as from 500 to 2,500 Daltons (e.g. from 500 to 2,000 Daltons, such as from 1,000 to 2,000 Daltons) or from 4,000 to 5,500 Daltons (e.g. from 4,000 to 5,000 Daltons).

Embodiments of the invention that may be mentioned include those in which the polymer of the invention is a compound selected from the list:

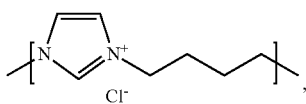

(i)

optionally wherein the number average molecular weight of the polymer is from 500 to 2,500 Daltons, such as from 500 to 2,000 Daltons;

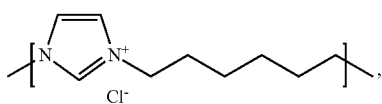

(ii)

optionally wherein the number average molecular weight of the polymer is from 500 to 2,500 Daltons, such as from 500 to 2,000 Daltons;

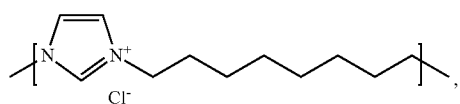

(iii)

optionally wherein the number average molecular weight of the polymer is from 500 to 2,500 Daltons, such as from 500 to 2,000 Daltons;

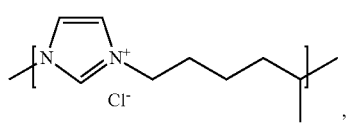

(iv)

optionally wherein the number average molecular weight of the polymer is from 500 to 2,000 Daltons;

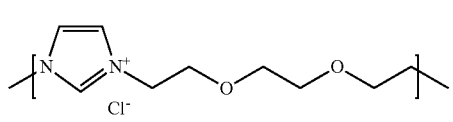

(v)

optionally wherein the number average molecular weight of the polymer is from 4,000 to 5,500 Daltons;

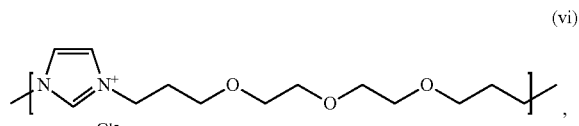

(vi)

optionally wherein the number average molecular weight of the polymer is from 4,000 to 5,000 Daltons; and

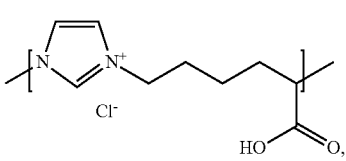

(vii)

optionally wherein the number average molecular weight of the polymer is from 500 to 2,000 Daltons.

In particular embodiments, the polymer of the invention may be selected from (i) to (vi) above, such as from (i) or (ii).

Embodiments of the invention that may be mentioned include those in which the copolymer of the invention is a compound selected from the list:

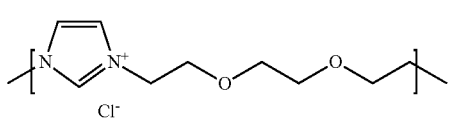

(i)

as the repeating unit of formula (I) and

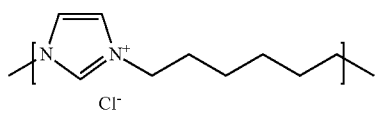

as the repeating unit of formula (II), optionally wherein the number average molecular weight of the copolymer is from 1,000 to 5,000 Daltons; and (ii)

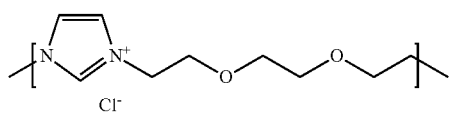

as the repeating unit of formula (I) and

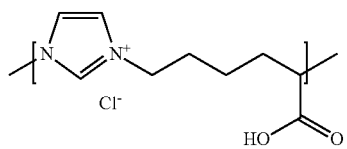

as the repeating unit of formula (II), optionally wherein the number average molecular weight of the copolymer is from 1,000 to 5,000 Daltons.

In certain embodiments of the invention that may be mentioned herein, the polymer or copolymer of the invention may be a polymer.

Further embodiments of the invention that may be mentioned include those in which the polymer or copolymer of the invention is isotopically labelled. However, other, particular embodiments of the invention that may be mentioned include those in which the polymer or copolymer of the invention is not isotopically labelled.

The term "isotopically labelled", when used herein includes references to polymers or copolymers of the invention in which there is a non-natural isotope (or a non-natural distribution of isotopes) at one or more positions in the compound. References herein to "one or more positions in the compound" will be understood by those skilled in the art to refer to one or more of the atoms of the polymer or copolymer of the invention. Thus, the term "isotopically labelled" includes references to compounds of the invention that are isotopically enriched at one or more positions in the polymer or copolymer.

The isotopic labelling or enrichment of the polymer or copolymer of the invention may be with a radioactive or non-radioactive isotope of any of hydrogen, carbon, nitrogen, oxygen, sulfur, fluorine, chlorine, bromine and/or iodine. Particular isotopes that may be mentioned in this respect include $^2H$, $^3H$, $^{11}C$, $^{13}C$, $^{14}C$, $^{13}N$, $^{15}N$, $^{15}O$, $^{17}O$, $^{18}O$, $^{35}S$, $^{18}F$, $^{37}Cl$, $^{77}Br$, $^{82}Br$ and $^{125}I$).

When the polymer or copolymer of the invention is labelled or enriched with a radioactive or nonradioactive isotope, polymer or copolymer of the invention that may be mentioned include those in which at least one atom in the compound displays an isotopic distribution in which a radioactive or non-radioactive isotope of the atom in question is present in levels at least 10% (e.g. from 10% to 5000%, particularly from 50% to 1000% and more particularly from 100% to 500%) above the natural level of that radioactive or non-radioactive isotope.

As noted above, the polymer or copolymer of the invention is in the form of the chloride salt. It has been surprisingly found that said salt is more effective than the acetate salt and is also surprisingly much less toxic to mammalian cells. It is unexpected that the change of counter ion would produce such a profound effect.

As noted above, the polymers and copolymers of the invention may be used in the treatment of microbial and fungal infections. Thus, there is also provided a pharmaceutical composition comprising the polymer or copolymer of the invention and a pharmaceutically acceptable carrier.

Polymers or copolymers of the invention may be administered by any suitable route, but may particularly be administered orally, intravenously, intramuscularly, cutaneously, subcutaneously, transmucosally (e.g. sublingually or buccally), rectally, transdermally, nasally, pulmonarily (e.g. tracheally or bronchially), topically, by any other parenteral route, in the form of a pharmaceutical preparation comprising the compound in a pharmaceutically acceptable dosage form. Particular modes of administration that may be mentioned include oral, intravenous, cutaneous, subcutaneous, nasal, intramuscular or intraperitoneal administration.

Polymers or copolymers of the invention will generally be administered as a pharmaceutical formulation in admixture with a pharmaceutically acceptable adjuvant, diluent or carrier, which may be selected with due regard to the intended route of administration and standard pharmaceutical practice. Such pharmaceutically acceptable carriers may be chemically inert to the active compounds and may have no detrimental side effects or toxicity under the conditions of use. Suitable pharmaceutical formulations may be found in, for example, Remington *The Science and Practice of Pharmacy*, 19th ed., Mack Printing Company, Easton, Pa. (1995). For parenteral administration, a parenterally acceptable aqueous solution may be employed, which is pyrogen free and has requisite pH, isotonicity, and stability. Suitable solutions will be well known to the skilled person, with numerous methods being described in the literature. A brief review of methods of drug delivery may also be found in e.g. Langer, *Science* (1990) 249, 1527.

Otherwise, the preparation of suitable formulations may be achieved routinely by the skilled person using routine techniques and/or in accordance with standard and/or accepted pharmaceutical practice.

The amount of the polymer or copolymer of the invention in any pharmaceutical formulation used in accordance with the present invention will depend on various factors, such as the severity of the condition to be treated, the particular patient to be treated, as well as the compound(s) which is/are employed. In any event, the amount of polymer or copolymer of the invention in the formulation may be determined routinely by the skilled person.

For example, a solid oral composition such as a tablet or capsule may contain from 1 to 99% (w/w) active ingredient; from 0 to 99% (w/w) diluent or filler; from 0 to 20% (w/w) of a disintegrant; from 0 to 5% (w/w) of a lubricant; from 0 to 5% (w/w) of a flow aid; from 0 to 50% (w/w) of a granulating agent or binder; from 0 to 5% (w/w) of an antioxidant; and from 0 to 5% (w/w) of a pigment. A controlled release tablet may in addition contain from 0 to 90% (w/w) of a release-controlling polymer.

A parenteral formulation (such as a solution or suspension for injection or a solution for infusion) may contain from 1 to 50% (w/w) active ingredient; and from 50% (w/w) to 99%

(w/w) of a liquid or semisolid carrier or vehicle (e.g. a solvent such as water); and 0-20% (w/w) of one or more other excipients such as buffering agents, antioxidants, suspension stabilisers, tonicity adjusting agents and preservatives.

Depending on the disorder, and the patient, to be treated, as well as the route of administration, polymers or copolymers of the invention may be administered at varying therapeutically effective doses to a patient in need thereof.

However, the dose administered to a mammal, particularly a human, in the context of the present invention should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Administration may be continuous or intermittent (e.g. by bolus injection). The dosage may also be determined by the timing or frequency of administration. In the case of oral or parenteral administration the dosage can vary from about 0.01 mg to about 1000 mg per day of a polymer or copolymer of the invention.

In any event, the medical practitioner, or other skilled person, will be able to determine routinely the actual dosage, which will be most suitable for an individual patient. The above-mentioned dosages are exemplary of the average case; there can, of course, be individual instances where higher or lower dosage ranges are merited, and such are within the scope of this invention.

The aspects of the invention described herein (e.g. the above-mentioned polymers and copolymers, methods and uses) may have the advantage that, in the treatment of the conditions described herein, they may be more convenient for the physician and/or patient than, be more efficacious than, be less toxic than, have better selectivity over, have a broader range of activity than, be more potent than, produce fewer side effects than, or may have other useful pharmacological properties over, similar compounds, combinations, methods (treatments) or uses known in the prior art for use in the treatment of those conditions or otherwise.

Polymers and copolymers of the invention may be prepared in accordance with techniques that are well known to those skilled in the art, for example as described hereinafter in the examples section.

Compounds of the invention may be isolated from their reaction mixtures using conventional techniques (e.g. recrystallisation, column chromatography, preparative HPLC, etc.).

The polymers and copolymers of the invention exhibit a pronounced antimicrobial action, especially against pathogenic gram-positive and gram-negative bacteria and so may also act against bacteria of skin flora, e.g. *Corynebacterium xerosis* (bacteria that cause body odour), and also against yeasts and moulds. They are therefore also suitable in the disinfection of the skin and mucosa and also of integumentary appendages (hair), and so may also be suitable in the disinfection of the hands and of wounds.

Given the above, the polymers and copolymers of the invention may be used as antimicrobial active ingredients in personal care preparations, for example shampoos, bath additives, hair-care products, liquid and solid soaps (based on synthetic surfactants and salts of saturated and/or unsaturated fatty acids), lotions and creams and other aqueous or alcoholic solutions, e.g. cleansing solutions for the skin.

Thus, there is also provided an antimicrobial and/or antifungal detergent composition comprising a polymer or copolymer of the invention and a surfactant. It will be appreciated that the composition may also contain additional cosmetically tolerable carriers and/or adjuvants. Said composition may in particular be in the form of a shampoo or in the form of a solid or liquid soap, though other compositions as described hereinabove are also contemplated (e.g. other hair-care products, lotions and creams etc.).

The detergent composition may comprise from 0.01 to 15% by weight, such as from 0.5 to 10% by weight of a polymer or copolymer of the invention. It will be appreciated that more than one polymer and copolymer of the invention may form part of the detergent composition.

Depending upon the form of the detergent composition, it will comprise, in addition to the polymer or copolymer of the invention, further constituents, for example sequestering agents, colourings, perfume oils, thickening or solidifying (consistency regulator) agents, emollients, UV absorbers, skin-protective agents, antioxidants, additives that improve mechanical properties, such as dicarboxylic acids and/or Al, Zn, Ca and Mg salts of $C_{14}$-$C_{22}$ fatty acids, and optionally preservatives.

The detergent composition may be formulated as a water-in-oil or oil-in-water emulsion, as an alcoholic or alcohol-containing formulation, as a vesicular dispersion of an ionic or non-ionic amphiphilic lipid, as a gel, a solid stick or as an aerosol formulation.

As a water-in-oil or oil-in-water emulsion, the detergent composition may comprise from 5 to 50 wt % of an oily phase, from 5 to 20 wt % of an emulsifier and from 30 to 90 wt % water. The oily phase may contain any oil suitable for cosmetic formulations, e.g. one or more hydrocarbon oils, a wax, a natural oil, a silicone oil, a fatty acid ester or a fatty alcohol. Preferred mono- or poly-ols are ethanol, isopropanol, propylene glycol, hexylene glycol, glycerol and sorbitol.

Detergent compositions may be provided in a wide variety of preparations. Examples of suitable compositions include, but are not limited to skin-care preparations (e.g. skin-washing and cleansing preparations in the form of tablet-form or liquid soaps, soapless detergents or washing pastes), bath preparations, (e.g. liquid compositions such as foam baths, milks, shower preparations or solid bath preparations), shaving preparations (e.g. shaving soap, foaming shaving creams, non-foaming shaving creams, foams and gels, preshave preparations for dry shaving, aftershaves or after-shave lotions), cosmetic hair-treatment preparations (e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, foams, hairsprays, bleaching preparations; e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or chamomile).

An antimicrobial soap may have, for example, the following composition:

0.01 to 5% by weight of a polymer or copolymer of the invention;
0.3 to 1% by weight titanium dioxide;
1 to 10% by weight stearic acid; and
the remainder being a soap base, e.g. the sodium salts of tallow fatty acid and coconut fatty acid or glycerol.

A shampoo may have, for example, the following composition:

0.01 to 5% by weight of a polymer or copolymer of the invention;
12.0% by weight sodium laureth-2-sulfate;
4.0% by weight cocamidopropyl betaine;
3.0% by weight NaCl; and
water to 100 wt %.

Non-limiting examples which embody certain aspects of the invention will now be described.

EXPERIMENTAL

Materials and Methods

Formaldehyde solution (37 wt %), glyoxal solution (40 wt %) and all diamines were purchased from Sigma-Aldrich. Acetic acid, L-lysine, 3-[4, 5-dimethylthiazol-2-yl]-2, 5-diphenyl tetrazolium bromide (MTT) were purchased from Alfa Aesar.

Bacteria strains used were *Escherichia coli* (ATCC 8739), *Staphylococcus aureus* (ATCC 29213), *Pseudomonas aeruginosa* (PAO1) *Acinetobacter Baumannii* (ATCC19606), *K. pneumoniae* (ATCC13883) and drug-resistant *Staphylococcus aureus* strains MRSA BAA40 and MRSA USA300, *Enterococcus faecalis* (OR1RF), vancomycin-resistant *Enterococcus faecalis* (VRE V583), multi-drug-resistance *Escherichia coli* (EC958) and *Enterobacter cloacae* (ATCC13047) were purchased from ATCC. Carbapenem-resistant (CR) and Multidrug-resistant (MDR) *P. aeruginosa* (PAER), CR and MDR *K. pneumoniae*, CR and MDR *A. baumannii* and clinical isolates of *Mycobacterium sp.* were acquired from Kevin Pethe's lab (Nanyang Technological University). All broth and agar were obtained from Becton Dickinson (BD) Company.

NMR spectra were obtained using a Bruker Avance DPX 300 instrument. Molecular weight distributions were measured with a Waters' gel permeation chromatography (GPC) system equipped with a 2410 refractive index detector (RID), using three ultrahydrogel columns in series and sodium acetate buffer (0.5 M of NaOAc and 0.5 M of AcOH, pH ~4.5) as mobile phase at 40° C. with a flow rate of 0.5 mL min$^{-1}$. The system was calibrated with a narrowly distributed pullulan standard. Fluorescence intensity of a sample was recorded on a LS5 Perkin-Elmer model spectrofluorometer equipped with stirring function.

Minimum Inhibition Concentration (MIC)

Minimum inhibition concentrations (MICs) were measured following standard broth dilution method with minor modification (Wiegand, I., et al., *Nat. Protoc.*, 2008, 3, 163-175). Briefly, subcultures of bacterial strains were grown overnight to mid-log phase, followed by an optical density (OD) check and dilution to reach a bacteria concentration of 5×10$^5$ CFU/mL. A two-fold serial dilution of the polymer solutions in Mueller Hinton Broth (MHB) media was carried out in a 96-well plate to obtain a series of concentrations. The bacteria suspension was then added into each well, except for two wells, one of which was the positive control (containing MHB media and the bacteria suspension without polymer) and the other the negative control (containing only sterilised MHB media). The plate was mixed in a shaker incubator for 10 min before it was transferred into a 37° C. incubator. The plate was incubated for 18 h, followed by OD measurement. The MIC value was noted as the lowest concentration for which 90% inhibition of bacteria growth was observed. Agar plating was also carried out to confirm the seeding bacteria concentration.

Hemolysis Test

Fresh human blood was collected from a healthy donor and used on the same day. Erythrocytes were concentrated via centrifugation and washed twice with a phosphate-buffered saline (PBS) buffer, followed by dilution to 5% v/v in PBS before use. A two-fold serial dilution of the polymer solutions was made in a 96 well plate, followed by the addition of the erythrocytes solution and incubation in a 37° C. shaker for 1 h with constant shaking at 150 rpm. The suspension was centrifuged (intact red blood cells settled at the bottom) and 80 μL of the supernatant was removed and added into a new 96-well plate. The sample was then mixed with 80 μL of PBS, and absorbance was measured at 540 nm using a microplate reader. Triton X-100 (1% in PBS buffer) was added for the positive control, and PBS solution was used for the negative control. The degree of haemolysis was determined using the following formula:

$$\% \text{ Haemolysis} = \left( \frac{A_{540} \text{ test sample} - A_{540} \text{ negative control}}{A_{540} \text{postive control} - A_{540} \text{negative control}} \right) \times 100$$

The haemolysis percentage was plotted against polymer concentration, and the HC$_{50}$ (concentration that causes 50% of erythrocytes to lyse) was determined via linear extrapolation. Two independent samples were measured for each experimental condition.

Cell Cytotoxicity Assay

The cell cytotoxicity assay was carried out on the 3T3 fibroblast cell line. Briefly, 3T3 cells were cultured in Dulbecco's Modified Eagle's Medium (DMEM) supplemented with 10% fetal bovine serum (FBS) and 1% antibiotics (penicillin/streptomycin) at 37° C. in an incubator supplied with 5% CO$_2$. The cells were harvested when 80% confluence was reached, and the cell concentration was counted using a hemocytometer. The cells were seeded in a 96-well plate at 1×10$^4$ cells per well and allowed to grow for 24 h. This was followed by treating the cells with various concentrations of the polymers for 24 h. The cell viability was then qualitatively evaluated with microscopy and quantified via MTT (3-(4, 5-dimethylthiazol-2-yl)-2,5-diphenyltetrazolium bromide) assay following the manufacturer's protocol. The cell viability was expressed as a ratio of cell population size treated with polymer compared to control (cells not treated with polymer). The data was analysed in triplicate and was obtained from three independent experiments.

To determine the IC$_{50}$ (concentration which reduces cell population by 50% with respect to control), each polymer was tested using the above protocol with eight concentrations ranging from 100 μg/mL to 1000 μg/mL and the resulting viability data was linearly regressed and/or fitted with sigmoid function and interpolated to get the IC$_{50}$ value. In further analyses nine concentrations ranging from 7.8 μg/mL to 2000 μg/mL with 2 fold increase were used in place of the eight concentrations, maintaining the rest of the protocol.

Example 1. Synthesis of PIM 1-7 as Chloride Salts

General Procedure for Synthesis of Imidazolium-Based Polymers

The following basic procedure was employed to prepare PIM 1-7. In a 100 mL round-bottom flask, aqueous solution of concentrated hydrochloric acid (37 wt %, 10.0 g, 100 mmol) was added dropwise to an aqueous solution of diamine (50 mmol in 10 mL of water) at 0° C. After 30 min, a mixture of formaldehyde (37 wt % in water, 2.31 g, 50 mmol) and glyoxal (40 wt % in water, 7.25 g, 50 mmol) was added dropwise to the above solution. Gradually, the color of solution changed from colorless to yellow. The reaction mixture was stirred for an additional 1 h at 80° C. Majority of the solvent and unreacted monomers was removed to give a yellow viscous oily liquid, which was diluted with water and dialysed with a dialysis bag (1 kDa cut-off) for 2 days.

PIM 1 Chloride

Treatment of concentrated hydrochloric acid (37 wt %, 10.0 g, 100 mmol) and diaminobutane (4.41 g, 50 mmol) with formaldehyde (37 wt % in water, 2.31 g, 50 mmol) and glyoxal (40 wt % in water, 7.25 g, 50 mmol) using the general procedure gave a yellow viscous oily liquid PIM 1 with 93% yield. $^1$H NMR (300 MHz, $D_2O$, 25° C. [ppm]): δ 8.84 (s, 1H, imidazole-H), 7.50 (s, 2H, imidazole-H), 4.24 (m, 4H, —$CH_2$—), 1.91 (m, 4H, —$CH_2$—).

PIM 2 Chloride

Treatment of concentrated hydrochloric acid (37 wt %, 10.0 g, 100 mmol) and 1,6-diaminohexane (5.81 g, 50 mmol) with formaldehyde (37 wt % in water, 2.31 g, 50 mmol) and glyoxal (40 wt % in water, 7.25 g, 50 mmol) using the general procedure gave a yellow viscous oily liquid PIM 2 with 94% yield. $^1$H NMR (300 MHz, $D_2O$, 25° C. [ppm]): δ 8.76 (s, 1H, imidazole-H), 7.47 (s, 2H, imidazole-H), 4.16 (t, 4H, —$CH_2$—), 1.85 (m, 4H, —$CH_2$—), 1.33 (m, 4H, —$CH_2$—).

PIM 3 Chloride

Treatment of concentrated hydrochloric acid (37 wt %, 10.0 g, 100 mmol) and 1,8-diaminooctane (7.21 g, 50 mmol) with formaldehyde (37 wt % in water, 2.31 g, 50 mmol) and glyoxal (40 wt % in water, 7.25 g, 50 mmol) using the general procedure gave a yellow viscous oily liquid PIM 3 with 93% yield. $^1$H NMR (300 MHz, $D_2O$, 25° C. [ppm]): δ 8.76 (s, 1H, imidazole-H), 7.47 (s, 2H, imidazole-H), 4.16 (t, 4H, —$CH_2$—), 1.84 (m, 4H, —$CH_2$—), 1.28 (m, 8H, —$CH_2$—).

PIM 4 Chloride

Treatment of concentrated hydrochloric acid (37 wt %, 10.0 g, 100 mmol) and 1,5-diamino-2-methylpentane (5.81 g, 50 mmol) with formaldehyde (37 wt % in water, 2.31 g, 50 mmol) and glyoxal (40 wt % in water, 7.25 g, 50 mmol) using the general procedure gave a yellow viscous oily liquid PIM 4 with 95% yield. δ 8.82 (s, 1H, imidazole-H), 7.48 (s, 2H, imidazole-H), 4.19 (m, 2H, —$CH_2$—), 3.92 (m, 1H, —CH—), 2.07-1.83 (m, 4H, —$CH_2$—), 1.40-1.19 (m, 2H, —$CH_2$—), 0.83 (s, 3H, —$CH_3$).

PIM 5 Chloride

Treatment of concentrated hydrochloric acid (37 wt %, 10.0 g, 100 mmol) and 2,2'-(ethylenedioxy)bis(ethylamine) (7.40 g, 50 mmol) with formaldehyde (37 wt % in water, 2.31 g, 50 mmol) and glyoxal (40 wt % in water, 7.25 g, 50 mmol) using the general procedure gave a yellow viscous oily liquid PIM 5 with 97% yield. $^1$H NMR (300 MHz, $D_2O$, 25° C. [ppm]): δ 8.86 (s, 1H, imidazole-H), 7.57 (s, 2H, imidazole-H), 4.42 (t, 4H, —N—$CH_2$—), 3.90 (t, 4H, —$CH_2$—$CH_2$—O), 3.68 (m, 4H, —O—$CH_2$—$CH_2$—O—).

PIM 6 Chloride

Treatment of concentrated hydrochloric acid (37 wt %, 10.0 g, 100 mmol) and 4,7,10-trioxa-1,13-tridecanediamine (11.0 g, 50 mmol) with formaldehyde (37 wt % in water, 2.31 g, 50 mmol), glyoxal (40 wt % in water, 7.25 g, 50 mmol) using the general procedure gave yellow viscous oily liquid PIM 6 with 97% yield. $^1$H NMR (300 MHz, $D_2O$, 25° C. [ppm]): δ 8.84 (s, 1H, imidazole-H), 7.52 (s, 2H, imidazole-H), 4.30 (t, 4H, —$CH_2$—), 3.65 (m, 8H, —O—$CH_2$—$CH_2$—O—), 3.55 (t, 4H, —$CH_2$—), 2.15 (m, 4H, —$CH_2$—).

PIM 7 Chloride

Treatment of concentrated hydrochloric acid (37 wt %, 10.0 g, 100 mmol) and L-lysine (7.2 g, 50 mmol) with formaldehyde (37 wt % in water, 2.31 g, 50 mmol), glyoxal (40 wt % in water, 7.25 g, 50 mmol) using the general procedure gave a yellow solid PIM 7 with 95% yield. $^1$H NMR (300 MHz, $D_2O$, 25° C. [ppm]): δ 9.11-8.77 (m, 1H, imidazole-H), 7.65-7.46 (m, 2H, imidazole-H), 5.13 (m, 1H, —CH—), 4.21 (m, 2H, —$CH_2$—), 2.32-1.77 (m, 4H), 1.26 (m, 2H, Discussion The PIM 1-7 chlorides were easily prepared from hydrochloric acid, a diamine, and a mixture of aqueous formaldehyde (37 wt %) and glyoxal (40 wt %) solution without the need for any organic solvents or inert gas via the Debus-Radziszewski reaction (FIG. 1). The polycondensation reactions proceeded efficiently at 80° C. with almost full consumption of the feed diamines and aldehydes in 90 min (Table 1). $^1$H NMR spectra of PIM 1-7 were recorded in $D_2O$. All the detected peaks can be clearly assigned to the corresponding protons of the anticipated product (FIG. 2a-g). The peaks around 8.75 and 7.45 ppm can be assigned to protons on the imidazolium rings, which confirmed the successful formation of the cationic five-membered imidazolium rings. GPC curves revealed that the obtained polymers have molecular weights ($M_n$) ranging from 1000 to 4700 Da and narrow molecular weight distributions ($M_w/M_n$) (1.13-1.22).

TABLE 1

Polymerisation of diamines, formaldehyde and glyoxal, in the presence of hydrochloric acid.

| Sample | Mole ratio of diamine: $CH_2O:(CHO)_2$ | T (° C.) | Time (min) | Water (wt %) | Mole of diamine (mmol) | $M_n{}^a$ (×$10^3$) | $M_w{}^a$ (×$10^3$) | PDI[b] | DP[c] |
|---|---|---|---|---|---|---|---|---|---|
| PIM 1 | 1:1:1 | 80 | 90 | 53 | 20 | 2.5 | 3.2 | 1.28 | 16 |
| PIM 2 | 1:1:1 | 80 | 90 | 53 | 20 | 1.1 | 1.5 | 1.33 | 6 |
| PIM 3 | 1:1:1 | 80 | 90 | 53 | 20 | 1.0 | 1.3 | 1.33 | 5 |
| PIM 4 | 1:1:1 | 80 | 90 | 53 | 20 | 1.1 | 1.6 | 1.41 | 6 |
| PIM 5 | 1:1.2:1 | 80 | 90 | 53 | 20 | 4.5 | 6.1 | 1.37 | 21 |
| PIM 6 | 1:1:1 | 80 | 90 | 53 | 20 | 1.9 | 2.6 | 1.36 | 7 |
| PIM 7 | 1:1:1 | 80 | 90 | 53 | 20 | 1.3 | 1.8 | 1.47 | 6 |

[a]GPC were conducted with water containing 0.5M NaOAc and 0.5M AcOH as the eluent, and calibrated using pullulan standards.
[b]PDI = polydispersity index
[c]DP = degree of polymerisation Example 2. Particle Sizes and Zeta Potential of PIM 1-7 Chlorides in Phosphate Buffered Saline (PBS)

The particle sizes and zeta potential values of the polymers in PBS were measured (Table 2). The hydrodynamic sizes for all PIMs were less than or around 2 nm in PBS buffer indicating that the polymers did not aggregate in PBS but remained as individual polymer chains. All polymers showed positive charges in PBS with a zeta potential ranging from +1 mV to +15 mV. With the increase of alkyl chain length from PIM 1 to PIM 3, a slight decrease in the zeta potential was observed and this was probably due to the decrease in charge density on the cationic imidazoliums with longer alkyl chain.

46, 8797-8807; Palermo, E. F., et al., *Biomacromolecules*, 2012, 13, 1632-1641). The increase in the hydrophobicity enhances the ability of the polymer potential to insert into bacteria membrane, therefore leading to better antimicrobial property.

However, a further increase the alkyl chain in PIM 3 did not improve its MIC value. This is probably due to the decreased fraction of charge in a repeated unit of the polymer, which reduces the interaction between the electrostatic charge on the polymer and the bacteria. As such, a longer alkyl chain spacer can make the electrostatic binding less efficient.

PIM 4 chloride was designed to have the same number of carbon atoms as that of PIM 2, but with a branched methyl group instead of a linear alkyl chain. A comparison of their

TABLE 2

Size and zeta potential measurements of PIM 1-7 in PBS buffer.

| Sample | Number Mean (d/nm) | Z-average (d/nm) | PDI | Mean Count Rate (kcps) | Zeta Potential (mV) |
|---|---|---|---|---|---|
| PIM 1 | 2.0 ± 0.1 | 360.4 ± 56.5 | 0.39 ± 0.06 | 320.6 ± 28.9 | 14.5 ± 0.7 |
| PIM 2 | 2.3 ± 0.1 | 724.8 ± 125.9 | 0.58 ± 0.17 | 304.5 ± 22.5 | 10.3 ± 0.3 |
| PIM 3 | 2.2 ± 0.8 | 1378 ± 330.9 | 0.86 ± 0.10 | 175.4 ± 47.9 | 8.7 ± 0.2 |
| PIM 4 | 1.9 ± 0.2 | 1205 ± 615.5 | 0.9 ± 0.2 | 208.2 ± 55.3 | 8.7 ± 0.7 |
| PIM 5 | 2.6 ± 0.3 | 424.8 ± 66.2 | 0.48 ± 0.06 | 107.1 ± 13.7 | 7.6 ± 0.6 |
| PIM 6 | 2.4 ± 0.2 | 845.1 ± 194.2 | 0.64 ± 0.05 | 103.1 ± 12.2 | 7.1 ± 1.0 |
| PIM 7 | 1.1 ± 0.3 | 1225.0 ± 379.6 | 0.77 ± 0.20 | 323.8 ± 179.0 | 1.4 ± 0.4 |

Example 3. Bactericidal Activities of PIM 1-7 Chlorides on Laboratory Bacteria Strains The effect of the hydrophilic/hydrophobic balance of PIM 1-7 chlorides on bactericidal activity was investigated as shown in Table 3, using the MIC protocol described above. The seven polymers were tested on a series of ESKAPE bacteria (*Enterococcus faecium, Staphylococcus aureus, Klebsiella pneumoniae, Acinetobacter baumannii, Pseudomonas aeruginosa*, and *Enterobacter* species), as well as some other bacteria.

PIM 1 chloride demonstrated antibiotic-like low minimum inhibitory concentrations (MICs) (<1 to 8 µg/mL) against all bacteria tested, including ESKAPE bacteria (e.g. Gram-positive *E. faecalis* (OG1RF) and *S. aureus* (ATCC 29213) as well as Gram-negative *K. pneumoniae* (ATCC 13883 and KPNS-1), *A. baumannii* (ATCC 19606), *P. aeruginosa* (PAO1, and pan-sensitive PAES-1), and *E. coli* (EC 8739)), as well as *Bacillus subtilis* (ATCC 6633).

PIM 2 chloride, which has a longer alkyl chain than PIM 1, gave slightly improved bactericidal activity than PIM 1. This is consistent with previously reported antibacterial polymer systems (Chin, W., et al., *Macromolecules*, 2013, performance showed that PIM 4 was less efficient than PIM 2, which may be due to the steric hindrance of the hydrophobic branched alkyl group.

To investigate the effect of hydrophobicity on bactericidal effect, PIM 5 chloride which contained the same number of carbon atoms as PIM 2 chloride, but with additional ether linkages, was synthesised. This relatively more hydrophilic PIM 5 (as compared to PIM 2) showed a significant decrease in bactericidal effect when the molecular weight was kept at around 2000 Da (PIM 5-1; Table 4, which was quite close to that of PIM 2 (Table 3). As the molecular weight increased to 4500 Da (PIM 5-2; Table 4), PIM 5 showed better bacteria killing properties.

A similar effect was also observed in PIM 6 chloride in which the hydrophilic portion led to poor bactericidal activity at lower molecular weight. The effect of alkyl group was further investigated by substituting the methyl group in PIM 4 with a carboxyl group in PIM 7 chloride. This modification resulted in an almost total loss of the bactericidal effect, indicating the importance of a hydrophobic portion to promote insertion into the bacteria membrane.

TABLE 3

Minimum inhibitory concentration ($MIC_{90}$, µg/mL) of PIM 1-7 chlorides on different laboratory and antibiotic-sensitive bacteria strains.

| | $MIC_{90}$ (µg/mL) | | | | | | | | |
|---|---|---|---|---|---|---|---|---|---|
| | Gram-positive | | | | Gram-negative | | | | |
| Sample | EF. OG1RF | SA 29213 | BS ATCC 6633 | EF 19489 | KP ATCC 13883 | AB ATCC 19606 | PAO1 | EC 8739 | EC13047 |
| PIM 1 | 8 | <1 | <1 | <1 | 4 | 2 | <1 | 4 | 2 |
| PIM 2 | 1 | <1 | <1 | <1 | 2 | 2 | 2 | 4 | 2 |

TABLE 3-continued

Minimum inhibitory concentration (MIC$_{90}$, μg/mL) of PIM 1-7 chlorides on different laboratory and antibiotic-sensitive bacteria strains.

| | MIC$_{90}$ (μg/mL) | | | | | | | | |
|---|---|---|---|---|---|---|---|---|---|
| | Gram-positive | | | | Gram-negative | | | | |
| Sample | EF. OG1RF | SA 29213 | BS ATCC 6633 | EF 19489 | KP ATCC 13883 | AB ATCC 19606 | PAO1 | EC 8739 | EC13047 |
| PIM 3 | 2 | 2 | <1 | 2 | 2 | 4 | 8 | 4 | 2 |
| PIM 4 | 16 | <1 | 2 | 4 | 4 | 4 | 8 | 8 | 8 |
| PIM 5 | 32 | 8 | 4 | 8 | 8 | 8 | 8 | 16 | 8 |
| PIM 6 | >256 | 256 | 64 | 256 | 64 | >256 | 256 | 256 | 512 |
| PIM 7 | >256 | 512 | 256 | >512 | >256 | >256 | >512 | >512 | >512 |

TABLE 4

GPC and MIC of PIM 5 chloride with various molecular weight

| | GPC | | | | MIC$_{90}$/(μg/mL) | | |
|---|---|---|---|---|---|---|---|
| Sample | M$_n$$^a$ (×10$^3$) | M$_w$$^a$ (×10$^3$) | PDI | DP | PAO1 | SA 29213 | EC 8739 |
| PIM 5-1 | 1.9 | 2.2 | 1.16 | 9 | 128 | 64 | 64 |
| PIM 5-2 | 4.6 | 6.3 | 1.36 | 21 | 8 | 8 | 8 |

$^a$GPC were conducted with water containing 0.5M NaOAc and 0.5M AcOH as the eluent, and calibrated using pullulan standards.

Example 4. Bactericidal Activities of PIM 1-7 Chlorides on Clinical Bacteria Strains To assess the potential of such PIM polymers for clinical applications (especially for broad-spectrum antimicrobial therapy), PIM 1-7 chlorides were tested on a range of drug-resistant strains including methicillin-resistant *S. aureus* (MRSA), vancomycin-resistant *Enterococcus faecalis* (VRE V583), multidrug-resistant *E. coli* (EC958), pan-resistant *P. aeruginosa* (PAER) and MDR *P. aeruginosa* (PAES, PAD25, PAD1 and PAW238), carbapenem resistant (CR) *K. pneumoniae* and CR *A. baumannii*, as shown in Tables 5 and 6.

Most of the polymers maintained similar killing potential as compared to the ATCC/laboratory strain, or in a similar order of magnitude. The PIMs retain a similar killing potential towards MRSA, *Pseudomonas aeruginosa* (PAO1) and *K. pneumonia*, though PIM 1 was slightly less effective (but in a similar order of magnitude) towards VRE583. The MIC data strongly suggest that PIMs are broad spectrum effective against both Gram-negative and Gram-positive bacteria. This property makes this class of polymers superior to some of the newly reported antimicrobial agents, which are active against either Gram-positive or Gram-negative bacteria, but not both (e.g. see Liu, Y., et al., *Angew. Chem. Int. Ed.* 2017, 56, 1486-1490; Ling, L. L., et al., *Nature*, 2015, 517, 455-459; Lam, S. J., et al., *Nat. Microbiol.*, 2016, 1, 16162). In addition, PIM 1 showed an antimicrobial effect comparable to a broader spectrum of bacteria than that of colistin, a last resort antimicrobial agent (Davis, S. D., *Antimicrob. Agents Chemother.*, 1975, 8, 50-53; Liu, Y.-Y., et al., *Lancet Infect. Dis.*, 2016, 16, 161-168).

TABLE 5

Minimum inhibitory concentration (MIC$_{90}$, μg/mL) of PIM 1-7 chlorides on various Gram-positive clinical bacteria strains.

| | MIC$_{90}$ (μg/mL) | | | |
|---|---|---|---|---|
| | Gram-positive | | | |
| Sample | EF. OG1RF | VRE 583 | MRSA BAA40 | MRSA USA300 |
| PIM 1 | 8 | 8 | <1 | <1 |
| PIM 2 | 1 | 1 | <1 | <1 |
| PIM 3 | 2 | 2 | 2 | 2 |
| PIM 4 | 16 | 4 | 2 | 2 |
| PIM 5 | 32 | 32 | 8 | 8 |
| PIM 6 | >256 | >256 | 256 | 256 |
| PIM 7 | >256 | >256 | 512 | 512 |

TABLE 6

Minimum inhibitory concentration (MIC$_{90}$, μg/mL) of PIM 1-7 chlorides on various Gram-negative clinical bacteria strains.

| | MIC$_{90}$ (μg/mL) Gram-negative | | | | | | | | | | |
|---|---|---|---|---|---|---|---|---|---|---|---|
| Sample | KPNS | KPNR | KPN | MRD AB-1 | AB ACBAS-1 | PA W238 | PA D1 | PA D25 | PA ER-1 | PA ES-1 | EC 958 |
| PIM 1 | 2 | 2 | 2 | 2 | 0.5 | <1 | <1 | <1 | <1 | <1 | 4 |
| PIM 2 | 1 | 1 | 2 | 2 | 1 | <1 | 2 | 4 | 2 | 2 | 4 |
| PIM 3 | 2 | 2 | 2 | 4 | 2 | 4 | 8 | 8 | 8 | 8 | <1 |
| PIM 4 | 4 | 4 | 2 | 4 | 2 | 8 | 16 | 16 | 16 | 16 | 8 |
| PIM 5 | 4 | 8 | 8 | 16 | 8 | 4 | 16 | 8 | 8 | 8 | 8 |
| PIM 6 | 32 | 128 | 64 | >256 | 128 | 256 | 512 | >512 | 512 | 256 | 128 |
| PIM 7 | >256 | >256 | >256 | >256 | >256 | 512 | >512 | >512 | >512 | >512 | >512 |

In addition, each PIM appear to have an effective range of molecular weight that allows them to function effectively in killing bacteria, and at the same time being less (or non-) toxic to mammalian cells. These weight ranges are summarised in Table 7 below.

TABLE 7

Effective range of molecular weight for PIM 1-7 chlorides

| Sample | Effective M$_n$ range |
|---|---|
| PIM 1 | 500 Da to 2.5 kDa |
| PIM 2 | Toxic across all M$_n$ tested |
| PIM 3 | Toxic across all M$_n$ tested |
| PIM 4 | 500 Da to 2.0 kDa |
| PIM 5 | 4 kDa to 5.5 kDa |
| PIM 6 | Not effective against bacteria |
| PIM 7 | Not effective against bacteria |

Example 5. Bactericidal Activities of PIM 1 Chloride on Various Mycobacteria MIC$_{50}$ were determined as previously described, with slight modifications. (*Nature Communications* 1 (2010): 57.) Briefly, compounds dissolved in DI water were twofold serial-diluted in duplicates and spotted by mosquito HTS (TTP LabTech) to 384-well clear plates, resulting in 10 dilutions of each compound. A volume of 50 μl of *M. tuberculosis* culture (final OD 600 of 0.02) was added to each well, and the assay plates were incubated at 37° C. for 5 days. OD600 values were recorded using a SpectraMax M2 spectrophotometer, and MIC$_{50}$ curves were plotted using GraphPad Prism 5 software. Under the assay setting, MIC$_{50}$ values, which fall in the linear part of the inhibition curve, are more robust and reproducible than MIC$_{90}$. Therefore, only MIC$_{50}$ values are reported in FIG. 3a-d.

Example 6. Hemolytic Property and Toxicity of PIM 1-7 Chlorides on Mammalian Cells The biocompatibility of the polymers was assessed based on the hemolytic property and toxicity of PIM 1-7 chlorides on mammalian cells. The concentrations of polymers that lysed 50% and 10% human red blood cells (HC$_{50}$ and HC$_{10}$ respectively) were measured using the protocols set out above. Remarkably, all polymers from PIM 1 chloride to PIM 6 chloride were not hemolytic even at 10 mg/mL (Tables 8a and b). The selectivity (HC$_{50}$/MIC) of all the antimicrobial PIMs are outstanding and the HC$_{50}$/MIC values even exceeded 10,000 for some bacteria strains. The hydrophobic components of the polymers were expected to lead to hemolysis, but surprisingly, PIM 1-2 chlorides and PIM 4-6 chlorides were shown to be non-hemolytic.

Figure 4:
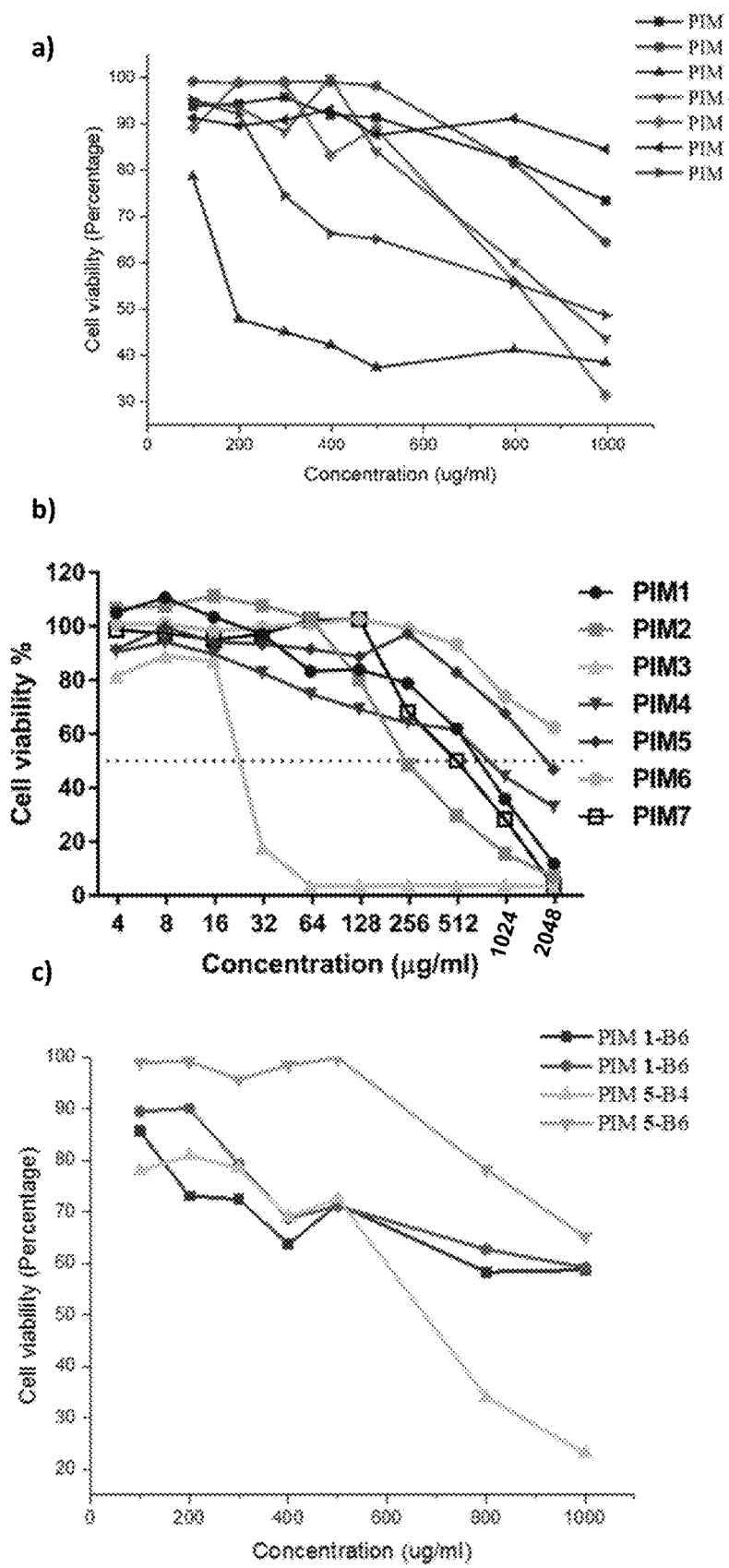
FIG. 4 Depicts the toxicity of (a-b) PIM 1-7 chlorides; and (c) different batches of PIM 1 and 5 chlorides, evaluated on 3T3 fibroblasts using MTT assay.

The toxicity of the PIM 1-7 chlorides was evaluated on 3T3 fibroblasts using the MTT assay described in detail above and the results are presented in Tables 8a and b and FIGS. 4a-c, Table 8 also incorporates the cell viability of the tested cells at 100 and 200 μg/mL. PIM 1 chloride gave a relatively high IC$_{50}$ (concentration of polymers that killed 50% of 3T3 fibroblast) and HC$_{50}$ (>10,000 μg/mL). PIM 3 chloride was shown to be the most cytotoxic as compared to PIM 1 chloride, which may be due to the increased backbone alkyl chain length in PIM 3 chloride. It is known that a longer alkyl chain length can make a polymer more toxic as the longer hydrophobic chain enhances membrane permeabilisation of the cationic surfactant-like imidazolium (Ranke, J., et al., *Ecotoxicol. Environ. Saf.*, 2004, 58, 396-404). On the other hand, PIM 1 chloride was shown to be relatively less toxic and this could be due to the lower molecular weight and the non-dangling hydrophobic alkyl nature of the polymer which prevents it from damaging the mammalian cells.

The introduction of ether linkages in the backbone of the polymers (in PIM 5 chloride and PIM 6 chloride) also greatly enhanced the biocompatibility (less toxic to cells) without sacrificing too much on the antibacterial efficacy. This may due to the increase in hydrophilicity of the PIM, which makes it interact less strongly with the cell membrane, therefore posing less toxicity to mammalian cells.

Table 8a represents the first analysis of the materials, which was then reproduced on multiple occasions and the more representative data is provided in Table 8b.

TABLE 8A

Hemolysis concentration (HC$_{50}$) (μg/mL) of PIM1-7 chlorides on human red blood cells and inhibitory concentration (IC$_{50}$, μg/mL) on 3T3 fibroblasts.

| Sample | HC$_{50}$ (μg/mL) | HC$_{10}$ (μg/mL) | IC$_{50}$ (μg/ml) |
|---|---|---|---|
| PIM 1 | >10,000 | >10,000 | 1536 |
| PIM 2 | >10,000 | >10,000 | 1271 |
| PIM 3 | >10,000 | 625 | 192 |
| PIM 4 | >10,000 | >10,000 | 919 |
| PIM 5 | >10,000 | >10,000 | 847 |
| PIM 6 | >10,000 | >10,000 | 1698 |
| PIM 7 | 1250 | 1250 | 954 |

TABLE 8B

Hemolysis concentration ($HC_{50}$) (μg/mL) of PIM1-7 chlorides on human red blood cells, and cell viability and inhibitory concentration ($IC_{50}$, μg/mL) on 3T3 fibroblasts.

| Sample | $HC_{50}$ (μg/mL) | $HC_{10}$ (μg/mL) | Cell viability (%) 100 μg/mL | Cell viability (%) 200 μg/mL | $IC_{50}$ (μg/ml) |
|---|---|---|---|---|---|
| PIM 1 | >10,000 | >10,000 | 74.53 | 69.51 | 670 |
| PIM 2 | >10,000 | >10,000 | 36.35 | 11.64 | 50 |
| PIM 3 | >10,000 | 625 | 10.40 | 6.92 | 20 |
| PIM 4 | >10,000 | >10,000 | 66.64 | 61.95 | 774 |
| PIM 5 | >10,000 | >10,000 | 91.72 | 90.61 | 1264 |
| PIM 6 | >10,000 | >10,000 | 95.20 | 93.45 | 1398 |
| PIM 7 | 1250 | 1250 | 74.53 | 69.51 | 525 |

Example 7. Outer Membrane Permeability of PIM 1-7 Chlorides on Bacteria

The bacteria outer membrane (OM) permeabilisation was investigated using hydrophobic 1-N-phenyl-naphthylamine (NPN) as a probe, following Hancock's protocol with minor modification (Loh, B., et al., *Antimicrob. Agents Chemother.*, 1984, 26, 546-551; Hancock, R., et al., *Antimicrob. Agents Chemother.*, 1991, 35, 1309-1314). Mid-log phase bacteria were pelleted and re-suspended in 5 mM HEPES buffer (pH=7.2) two times to remove the previous medium and nutrients thoroughly. Bacteria suspension with OD of 0.2 was incubated with NPN reagent (diluted in HEPES buffer) in the wells of a black 96-well culture plate for a few minutes to get stable fluorescence intensity. Polymer solutions with various concentrations were added into each well and quickly mixed with a multichannel pipette. The fluorescence intensity was recorded using a Tecan microplate reader. The final concentration of NPN was kept at 10 μM, and at least 6 concentrations were measured for each polymer.

Figure 5:
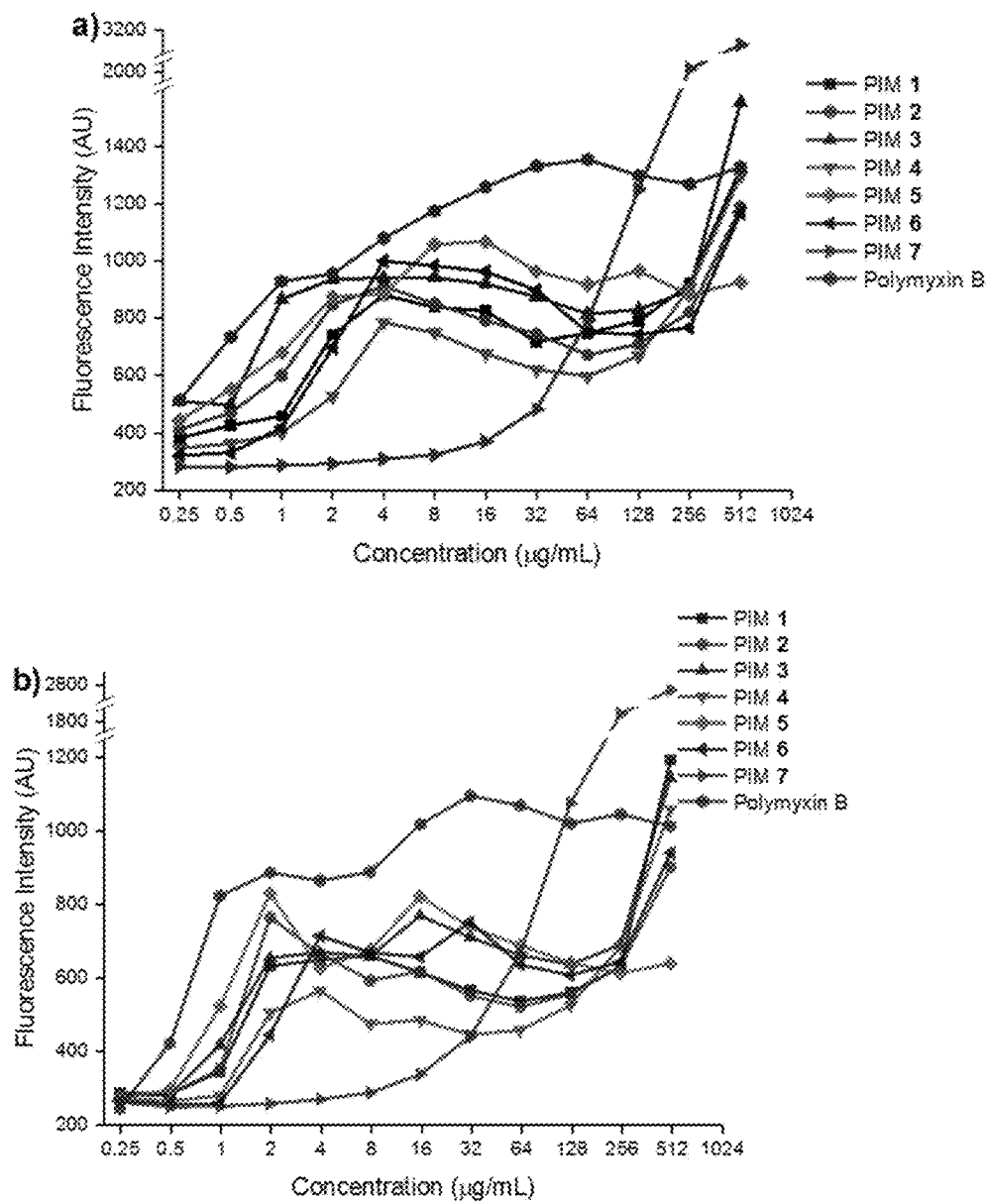
FIG. 5 Depicts the outer membrane permeability assay of PIM 1-7 chlorides, evaluated on (a) EC8739; and (b) PAO1 bacteria, using 1-N-phenyl-naphthylamine (NPN) as the fluorescence probe. Polymixin B was used as a reference.

The killing mechanism of the polymers was verified using the bacteria outer membrane (OM) permeability assay described above, using 1-N-phenyl-naphthylamine (NPN) as the fluorescence probe. NPN being hydrophobic, fluoresces weakly in an aqueous environment, but gives strong fluorescence signals in a hydrophobic environment. Any compounds that permeabilise the OM of the bacteria can enhance NPN uptake, such that more NPN can partition into the hydrophobic membrane interior, leading to higher fluorescence intensity (Loh, B., C. Grant, and R. Hancock, *Antimicrob. Agents Chemother.*, 1984, 26, 546-551). The PIM chlorides were tested against two Gram-negative strains, *E. coli* (EC8739) and *P. aeruginosa* (PAO1) (FIG. 5a-b). PIM 1-4 chloride showed good membrane permeabilisation against both strains at around MIC concentration and above, but become poor at sub-MIC concentration (FIG. 5a-b). This follows the same trend as the well-studied antibiotic, Polymyxin B. OM can be disturbed via membrane component biosynthesis inhibition, physical damage or lipopolysaccharides (LPS) disorganisation etc (Vaara, M., *Microbiol. Rev.*, 1992, 56, 395-411). In this case, PIM 1-4 chlorides may act as a polycation moiety that can bind to anionic LPS and disorganise its OM structure, leading to enhanced uptake of NPN.

For PIM 5-7 chlorides, a concentration dependent-fluorescence intensity was also observed. However, it was noted that PIM 7 quickly lost the ability to permeabilise the OM when its concentration dropped to 32 μg/mL and below. It is worth noting that while PIM 7 chloride has no bacteria killing activity, it can permeabilise the OM fairly well. This is probably due to the pendant carboxyl group on the backbone which may bind to $Mg^{2+}$ and $Ca^{2+}$ ions to disorganise the LPS leading to an uptake of NPN fluorescence probe. Though the cationic imidazolium charge on the PIM 7 backbone can still bind to LPS, the negative carboxyl group can repel the polyanionic LPS which reduces the ability of the polymer to penetrate the bacteria OM deeply. This is likely to result in low extent of LPS disorganisation and hence poor bactericidal activity.

Example 8. Inner Membrane Depolarisation of PIM 1-7 Chlorides on Bacteria

Membrane potential-sensitive dye, 3,3'-Dipropylthiadicarbocyanine Iodide ($DiSC_3(5)$), was used to determine the effect of the polymers on bacteria inner membrane depolarisation. This was carried out following Hancock's protocol with minor modifications (Zhang, L., et al., *Antimicrob. Agents Chemother.*, 2000, 44, 3317-3321). Bacteria cells in mid-log phase were pelleted by centrifugation and re-suspended in 5 mM HEPES buffer supplied with 100 mM KCl in order to equilibrate the cytoplasmic and external $K^+$ concentrations. A stock cell suspension was prepared by diluting the as-prepared cell suspension 20-fold to an OD of around 0.2. $DiSC_3(5)$ solution was then added to provide $DiSC_3(5)$ in a concentration of 100 nM in the stock solution. 2 mL of the stock cell suspension was placed into a quartz cuvette (pathlength of 1 cm) and equilibrated, followed by the addition of the polymer solution to provide a concentration of a 100 μg/mL of polymer. Fluorescence intensity changes due to membrane potential gradient disruption were continuously recorded with a Perkin-Elmer LS55 model Fluorescence Spectrometer.

Inner membrane (IM) depolarisation was evaluated with the $DiSC_3(5)$ fluorescence assay described in detail above. Generally, an electrical potential gradient (Δψ of −140 mV) generated by trans-cytoplasmic membrane proton motive force is stable, provided that the impermeability of the membrane to ions is not compromised by the study compound. This can be easily evaluated using $DiSC_3(5)$ as a fluorescence probe. Firstly, $DiSC_3(5)$ was incubated with the bacteria suspension to allow it to be taken up into the bacteria IM according to the magnitude of electrical potential gradient, and self-quenched its fluorescence. When Δψ is depolarised by a compound, $DiSC_3(5)$ dye will be released from the IM, leading to an increase in the fluorescence intensity (Zhang, L., et al., *Antimicrob. Agents Chemother.*, 2000, 44, 3317-3321). For Gram-negative bacteria, the OM was first permeabilised using 0.2 mM ethylenediaminetetraacetic acid (EDTA) to allow the up-take of $DiSC_3(5)$ dye into the IM. This was then followed by procedures similar to that of the Gram-positive bacteria.

Figure 6:
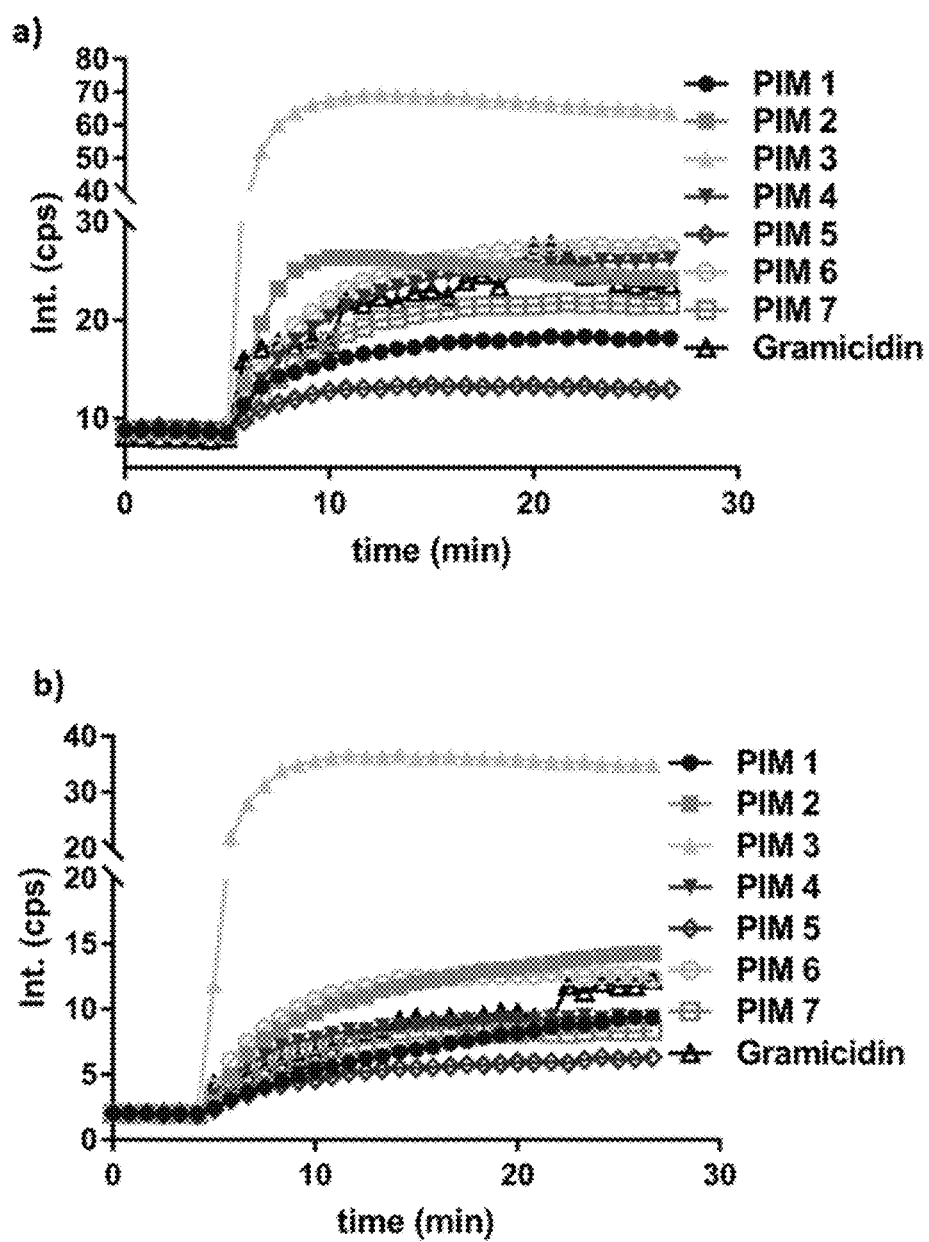
FIG. 6 Depicts the inner membrane potential assay of PIM 1-7 chlorides evaluated on (a) MRSA USA300; and (b) EC8739, using $DiSC_3(5)$ as the fluorescence probe. The concentration of the polymers and gramicidin (reference) was 100 μg/mL.

For both Gram-positive bacteria MRSA USA300 and Gram-negative bacteria EC8739, the PIM 1-3 chlorides were shown to easily permeabilise the IM, leading to an increase of fluorescence intensity (FIG. 6a-b). The ability to depolarise Δψ increases with increase of the hydrophobic alkyl chain length. This is clearly evident in PIM 3 chloride, which induced a drastic increase in fluorescence intensity within a few minutes that was greater than that of the positive control, gramicidin. PIM 4 chloride showed relatively poorer IM disruption as compared to PIM 2 chloride (same number of carbons as PIM 4, but with a linear alkyl chain), and this correlates well with their bactericidal property. For PIM 5 chloride and PIM 6 chloride, the poor IM disruption could be due to the increase in their hydrophilicity which led to poorer ability to interfere with the bacteria IM.

Example 9. Synthesis of Sulforhodamine B-Conjugated PIM 1 and 5 and Evaluating their Interaction with Bacteria Via Stimulated Emission Depletion (STED) Microscopy As the PIM synthesis scheme used herein is similar to a 2A+B polycondensation reaction, the end group was expected to be a protonated amine, since the reaction was conducted in an acidic environment. To confirm this NMR in deuterated DMSO was conducted on PIM 1 chloride and a clear new peak at 8.36 ppm was obtained, which corresponds to the end-amine hydrochloride salt. We used this end amine group to conjugate one rhodamine derivative dye molecule to PIM 1 and PIM 5 for STED imaging.

Figure 7:
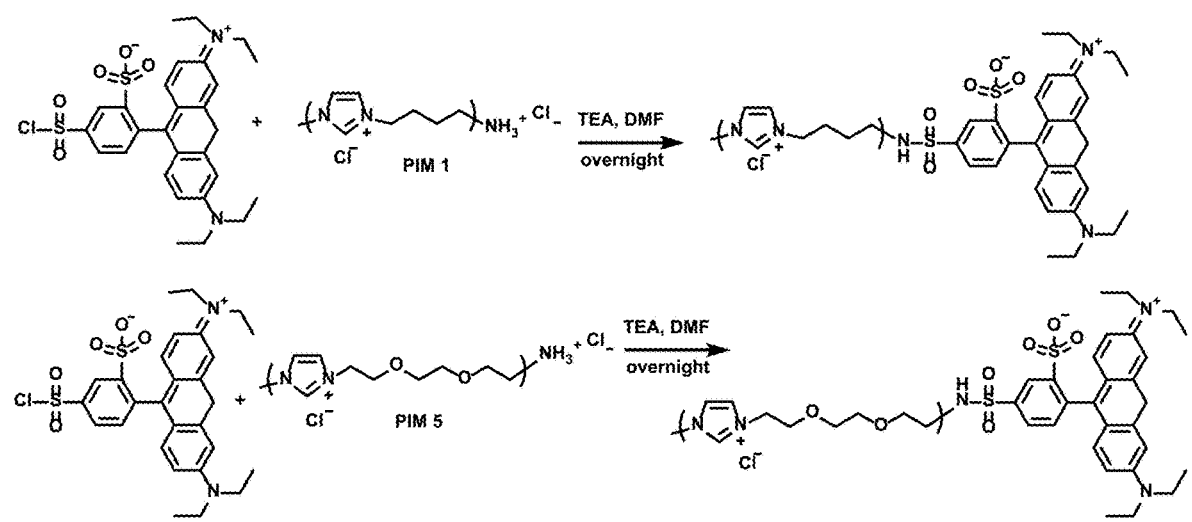
FIG. 7 Depicts the synthesis of sulforhodamine B-PIM 1 and PIM 5 conjugates.

To directly visualise the interaction of the polymer with the microbes via Stimulated Emission Depletion (STED) microscopy, conjugates of sulforhodamine B with PIM 1 and PIM 5 were synthesised by conjugating the amine end of the polymer chain to the sulfonate group, as shown in FIG. 7. Briefly, to a DMF solution of PIM 1, 2.5 equivalents triethylamine (TEA) was first added to remove the hydrochloride acid on the amine end of the polymer chain. Sulforhodamine B acid chloride (1.2 equivalent) was then introduced to the above solution and stirred overnight in a dark environment. The solution was then dialysed for 2 days to fully remove the salts and residual dye. This was followed by lyophilisation to give the final sulforhodamine B-PIM 1 conjugate. The synthesis for sulforhodamine B-PIM 5 conjugate follows a procedure similar to the above.

To prepare the samples for visualisation, a single colony from an agar plate was picked to culture overnight in MHB medium, followed by subculture to reach exponential phase. The bacteria was pelleted and washed with PBS twice before being adjusted to a concentration of $1 \times 10^8$ CFU/mL. This was then added into a desired concentration (i.e. 0.5×MIC, 1×MIC, and 2×MIC) of sulforhodamine B-conjugated polymer and incubated for 2 h. The labelled bacteria suspension was then washed once with PBS, followed by fixing in 4% paraformaldehyde for 30 min. The cells were then washed twice with PBS and then incubated with FM1-43FX membrane dye for 10 min on ice. The cells were again washed with PBS twice and then sealed in slides using nail polish, before they were imaged via STED microscopy.

Figure 8:
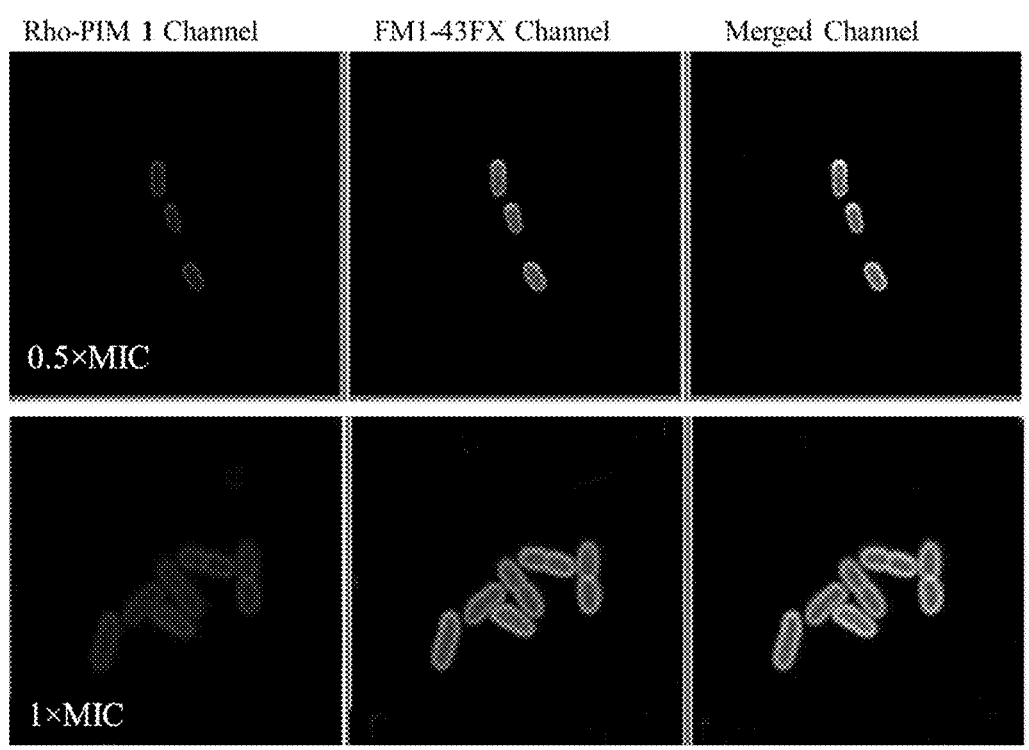
FIG. 8 Depicts the STED fluorescence images of PAO1 treated with sulforhodamine B-PIM 1 conjugate at various concentrations.
Figure 9:
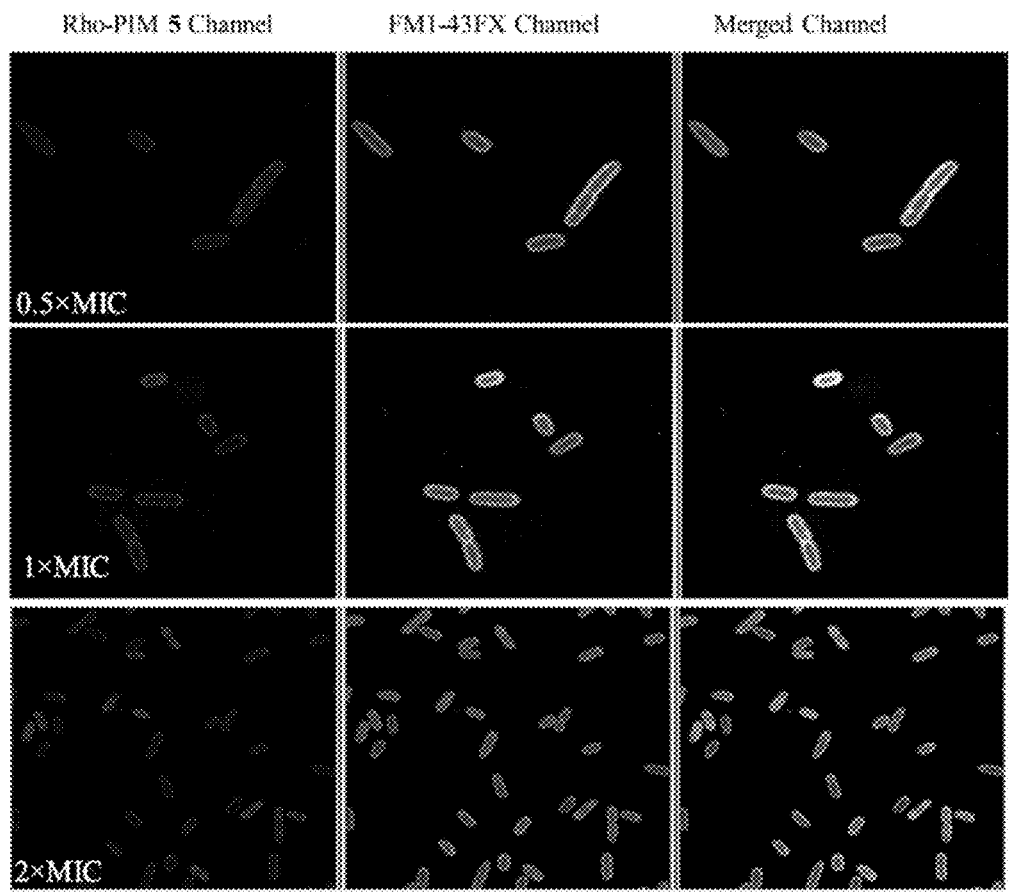
FIG. 9 Depicts the STED fluorescence images of PAO1 treated with sulforhodamine B-PIM 5 conjugate at various concentrations.

Fluorescence images of *Pseudomonas aeruginosa* (PAO1 labelled with FM1-43FX membrane dye) treated and not treated with sulforhodamine B-PIM 1 and PIM 5 conjugates (at a concentration range approximately equal to 0.5×MIC, 1×MIC and 2×MIC) are as shown in FIGS. 8 and 9. A clear colocalisation of the sulforhodamine B-polymer conjugates and membrane dye was observed at 0.5×MIC. At higher concentrations, the PIM 1 conjugate lysed the cell membrane and entered into the cytoplasm, resulting in a substantial penetration into the cytosol in a significant fraction of the cells. This suggests that PIM 1 first binds to bacteria membrane via electrostatic interaction, followed by causing further penetration and damages to the membrane.

Figure 10:
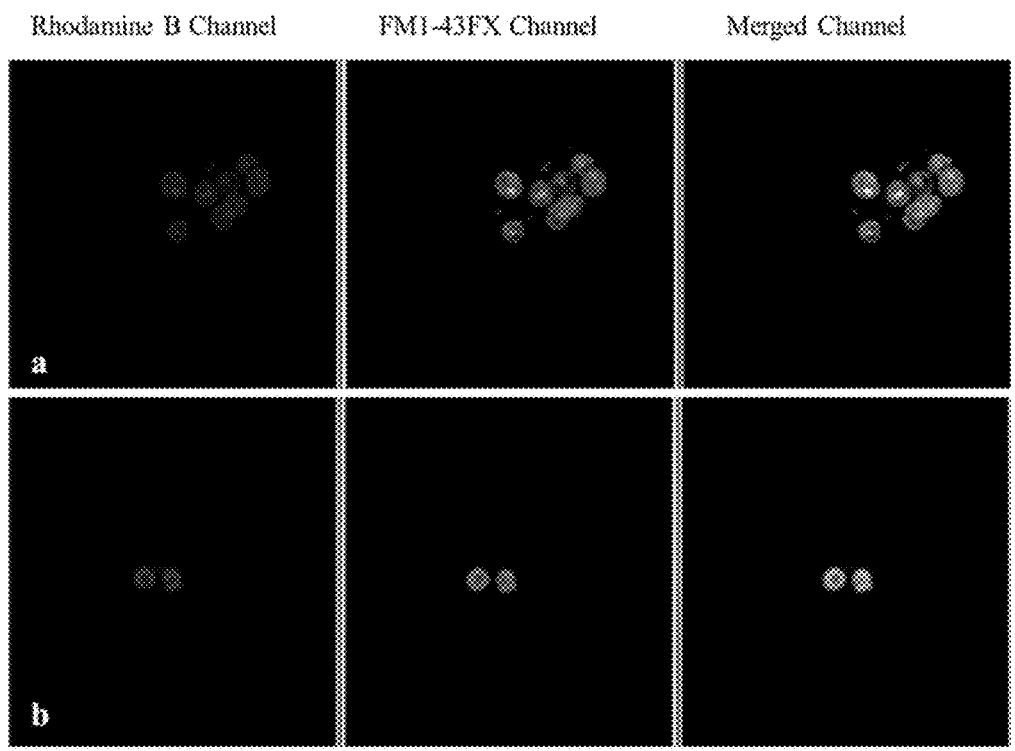
FIG. 10 Depicts the STED fluorescence images of (a) PIM 1 chloride and (b) PIM 5 chloride on MRSA USA300 at a concentration of 0.5×MIC.

For the PIM 5 conjugate, even at a low 0.5×MIC concentration, the polymer was found to be both on the surface and within the bacteria cells, demonstrating its better ability to penetrate the bacteria membrane (FIG. 9). This is probably due to the ether groups in PIM 5 which favor hydrogen bonding with the membrane lipid of PAO1. At higher concentration, the polymers showed greater damage to the membrane, therefore resulting in more conjugates entering into the cytosol. Super-resolution STED microscopy with MRSA USA300 was also conducted (FIG. 10), and a similar colocalisation effect was observed.

Example 10. Evaluating the Killing Kinetics of PIM 1 and PIM 5 Chloride on PAO1 and MRSA USA300 Bacteria PIM 1 chloride and PIM 5 chloride with final concentrations of 4×, 2×, 1× and 0.5×MIC were incubated with exponential phase PAO1 and MRSA USA300 cells with constant shaking. Aliquots of the suspensions were taken at different time points (5, 15, 30, 45, 60, 90 and 120 min) to determine the CFU/mL using spot plating method. Two independent experiments were performed for each polymer/pathogen combination.

Figure 11:
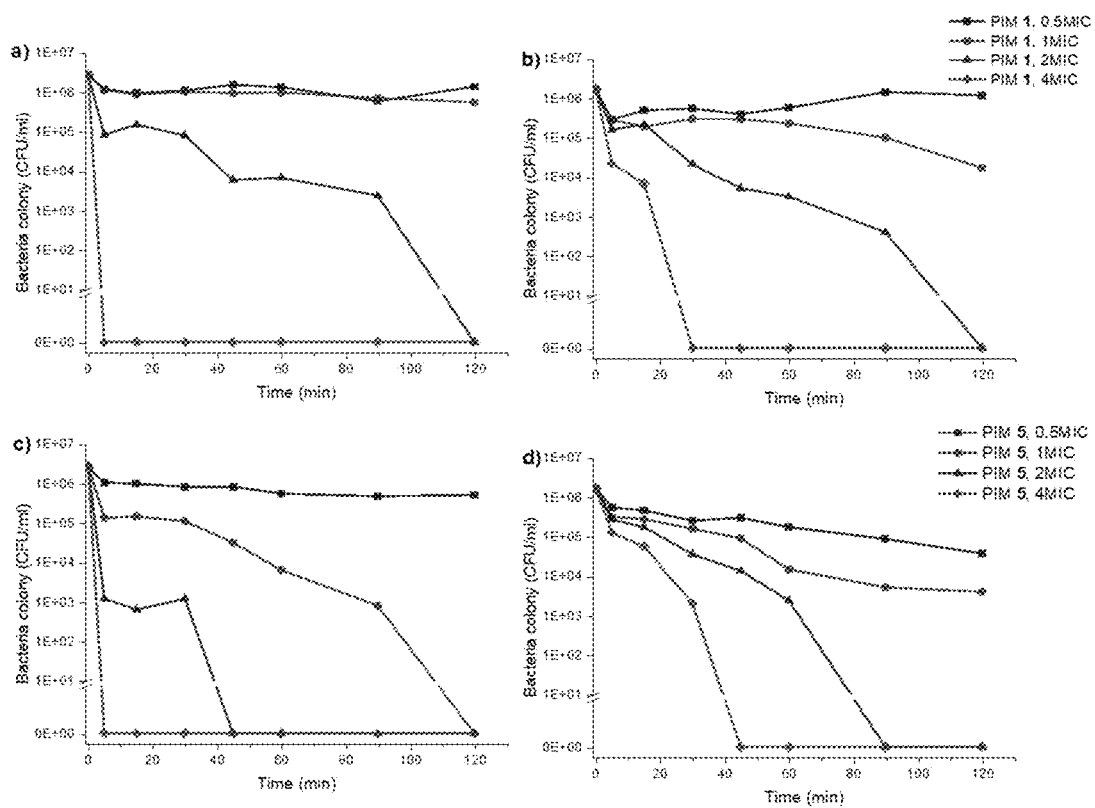
FIG. 11 Depicts the bacteria killing kinetics of (a) PIM 1 chloride and (c) PIM 5 chloride on PAO1; and (b) PIM 1 chloride and (d) PIM 5 chloride on MRSA USA300.

The bacteria killing kinetics as shown in FIGS. 11a and c demonstrated that both PIM 1 chloride and PIM 5 chloride can kill PAO1 at an extremely fast rate. At 4×MIC concentration, both PIM 1 and 5 chloride can eliminate almost all of PAO1 within 5 min, demonstrating that such PIMs are bactericidal rather than bacteriostatic. PIM 1 chloride and PIM 5 chloride killed drug-resistant MRSA USA300 more slowly, but more than 99.99% of killing was observed in less than 45 min (FIGS. 11b and d).

Example 11. Resistance Evolution of SA29213 in the Presence of PIM 1 and 5 Chloride To test for development resistance by sequential passage, SA ATCC 29213 at exponential phase was diluted to $1 \times 10^7$ CFU/mL in 1 mL MHB medium containing different concentrations of polymer (2×, 1× and 0.5×MIC), followed by incubating at 37° C. with constant shaking (Ling, L. L., et al., Nature, 2015, 517, 455-459). Bacteria growth was monitored at 24 h intervals and cultures from media contain the highest concentration of polymer that allowed bacteria growth ($OD_{600} > 0.2$) were diluted 1:100 with fresh media containing 2×, 1×, and 0.5×MIC polymer. Resistance was evaluated for 21 days (or longer), until a significantly high value of $MIC/MIC_{original}$ was reached. Aliquots of the bacteria at various time points were stored in glycerol and kept at −80° C. for further study whenever resistance development was observed. Ofloxacin was used as the positive control.

Figure 12:
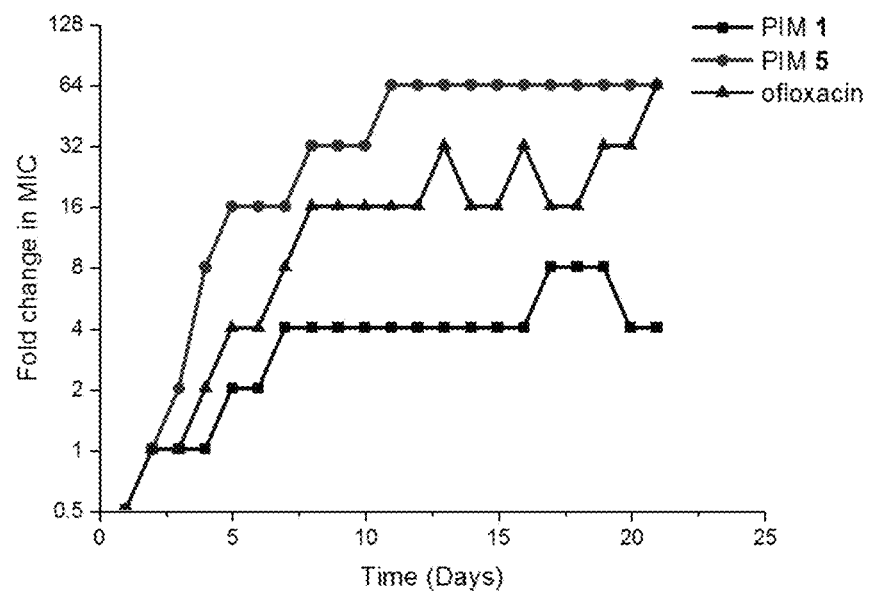
FIG. 12 Depicts the resistance evolution of *S. aureus* (SA29213) via serial passaging in the presence of sub-MIC concentrations of PIM 1 chloride, PIM 5 chloride and ofloxacin (positive control).

Resistance evolution was determined via serial passaging of SA29213 in the presence of sub-MIC levels of PIM 1 chloride, PIM 5 chloride and ofloxacin (as positive control) continuously for 21 days (FIG. 12). For ofloxacin control, the resistance evolved to above 128 MIC fold change. Although PIM 1 and 5 chlorides can kill bacteria non-specifically, the bacteria treated with PIM 5 chloride quickly developed resistance in ten days. On the other hand, the bacteria treated with PIM 1 chloride developed very mild resistance only after ten days, and the MIC value was low and within clinical dosage range. This was surprising, as it is known to be difficult for bacteria to develop resistance towards non-specific killing compound. As such, it is deduced that PIM 1 chloride and PIM 5 chloride kill different bacteria via different mechanisms or via a multimodal mechanism.

Example 12. In Vivo Efficacy of PIM 1 Chloride on Mouse Septicemia Model

Figure 13:
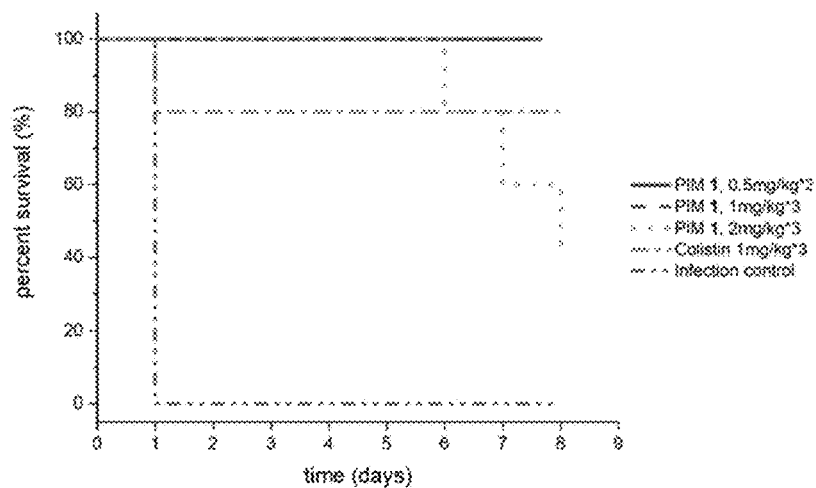
FIG. 13 Depicts the percentage survival rate of mice in the PAO1 mouse septicemia model in the presence of various active agents and doses. At 0.5 h, 4 h and 8 h post-infection time points, PIM 1 chloride was introduced by intraperitoneal injection at concentrations of 0.5 mg/kg, 1 mg/kg and 2 mg/kg for different test groups (5 mice per group). For the positive control, 1 mg/kg of colistin with each dosage at the exactly same time points was administered.

Given the excellent bacteria killing properties and biocompatibility of PIM 1 chloride, the therapeutic efficacy of this polymer was tested in vivo using a mouse septicemia model (FIG. 13). Balb/c female mice (7 weeks with one week quarantine) were used to test the PAO1 septic shock protection efficacy of PIM 1. Exponential phase of PAO1 was collected and washed twice with PBS, and re-suspended in the same volume of PBS. 300 μL of cell suspension containing $3\times10^7$ CFU of PAO1 was introduced into each mouse via intraperitoneal injection to induce septic shock. The mice (5 per group) were treated with three exact IP dosages of 0.25 mg/kg, 0.5 mg/kg and 1 mg/kg PIM 1 at 0.5 h, 4 h and 8 h post-infection, Positive and negative control groups of mice were injected with 1 mg/kg of collistin and same volume of PBS respectively, at the same time points. The survival rate of the mice was monitored over 7 days.

More than 90% of the mice in the negative control group died within 24 h after being infected with PAO1. The mice treated with colistin only had an 80% survival rate, while all mice treated with 0.5 mg/kg and 1 mg/kg of PIM 1 chloride survived without obvious negative side effects.

In another study, mice (5 per group) were treated with varied doses of PIM 1 at 1 h, 4 h and 8 h post-infection with PAO1. Positive and negative control groups of mice were injected with 2 mg/kg of imipenem and same volume of PBS respectively, at the same time point. At the 12th hour, all mice were euthanized with peritoneal washes performed via injecting 3.0 mL of PBS into the intraperitoneal cavity followed by massaging the abdomen for 1 min. After which, approximately 1 mL of peritoneal fluid was recovered to calculating the CFU of bacteria, as well as for immune cells quantification. Bacterial loads were also evaluated in the spleen, liver and kidneys of the animals.

For carbapenem-resistant *Acinetobacter baumannii* (CRAB) and carbapenem-resistant *Pseudomonas aeruginosa* (CRPA) septicemia protection model, similar procedure was conducted with care and 5% mucin was injected together with the bacteria to have the mice immunocompromised (resulting in similar conditions as hospitalised patients). The amount of bacteria was analysed with one-way classification analysis of variance (ANOVA) and student's t-test (Graphpad Prism for Windows, version 7). For the infection controls without any treatment, the animals were sacrificed within 12 h, since they were all moribund.

For the quantification of PAO1 CFU in the peritoneal fluid, PIM 1 chloride was administered via the intraperitoneal route with one of the two dosing regimes—either three-dose each of 2 mg/kg of PIM 1 chloride at 1, 4, and 8 h post-infection or a single dose of 6 mg/kg 1 h post-infection. The control antibiotic used was imipenem with 2 mg/kg administered with 3 doses (1, 4, and 8 hours post-infection). The mice were euthanised 12 h post-infection and the amount of PAO1 in the intraperitoneal fluid was analysed. For both treatment regimes, PIM 1 chloride resulted in a 5-order reduction in the PAO1 bacteria population in the peritoneal fluid (FIG. 14a) as compared to the negative control. In addition, it was observed that PIM 1 chloride was as effective as imipenem.

Figure 14:
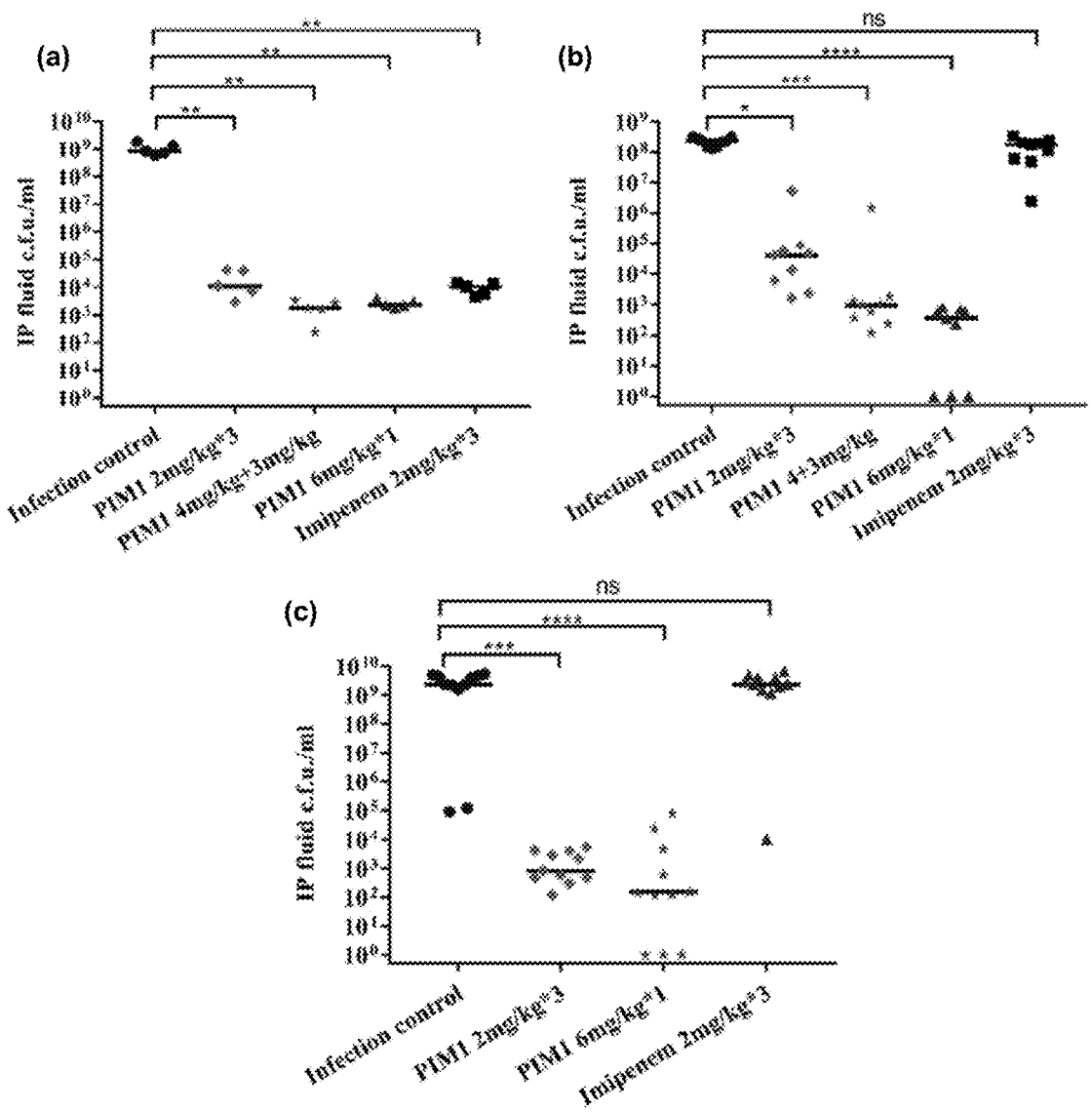
FIG. 14 Depicts the bacteria colony (CFU) in the peritoneal fluid of mice used in a mouse septicemia model infected with (a) PAO1; (b) PAER; and (c) AB-1, with various active agents and dosages. PIM 1 chloride was administered via the intraperitoneal route with one of the two dosing regimens—either three-doses each of 2 mg/kg of PIM 1 at 1, 4, and 8 h post-infection or a single dose of 6 mg/kg 1 h post-infection. The control antibiotic used was 2 mg/kg imipenem administered with three doses (1, 4, and 8 hours post-infection).

The efficacy of PIM 1 chloride was next tested against PAER (a carbapenem-resistant *Pseudomonas aeruginosa* (CRPA) bacteria strain) with the in vivo peritoneal septicemia model. With a carbapenem (e.g. imipenem) as the antibiotic control, no reduction in the population of CRPA in the intraperitoneal fluid was observed and the mice became moribund within 12 h post-infection (FIG. 14b). With PIM 1 chloride, excellent bacterial clearance of 3.75 and 5.80 orders of CRPA in the intraperitoneal was achieved using 6 mg/kg (1 dose) and 2 mg/kg (3 doses) respectively.

The efficacy of PIM 1 chloride was also tested on AB-1 (a carbapenem-resistant *Acinetobacter baumannii* (CRAB) strain) which is a critical bacteria that requires the attention for new antibiotics. Similar to PAER, the positive control imipenem did not show any removal of AB-1 from the peritoneal fluid in comparison to the infection control (FIG. 14c). PIM 1 chloride was shown to be effective in eradicating the AB-1 in vivo. For the similar dosing regime as imipenem (i.e. 2 mg/kg×3 doses), the infected mice treated with PIM 1 chloride showed a significant reduction of bacteria by 6.46 orders of magnitude in the peritonea fluid (FIG. 14c). Similarly, excellent reduction by 7.20 orders was achieved with the single dose treatment.

Example 13. In Vivo Efficacy of PIM 1 Chloride on Mouse Skin Infection Model

The potential of PIM 1 chloride as a topical drug was also evaluated. CRAB and CRPA are often associated with open wounds, which can dramatically slow down the healing process.

To evaluate the potency of PIM 1 chloride in a wound model, a wound on the back skin of the shaved mice was created using biopsy punch prior to introducing the bacteria. $10^6$ CFU of bacteria (wild type PAO1, CRAB or CRPA) was introduced via pipetting on the top of wound and immediately covered with a layer of Tegaderm. At the $4^{th}$ h infection time point, antimicrobial treatment was applied by injecting the polymers or antibiotics beneath the Tegaderm layer, followed by covering the wound with another layer of Tegaderm. After 24 h of treatment, a 1×1 cm square mice skin with wound in the center was harvested, homogenised, followed by plating. PBS was used as the negative control and imipenem was used as the positive control.

Figure 15:
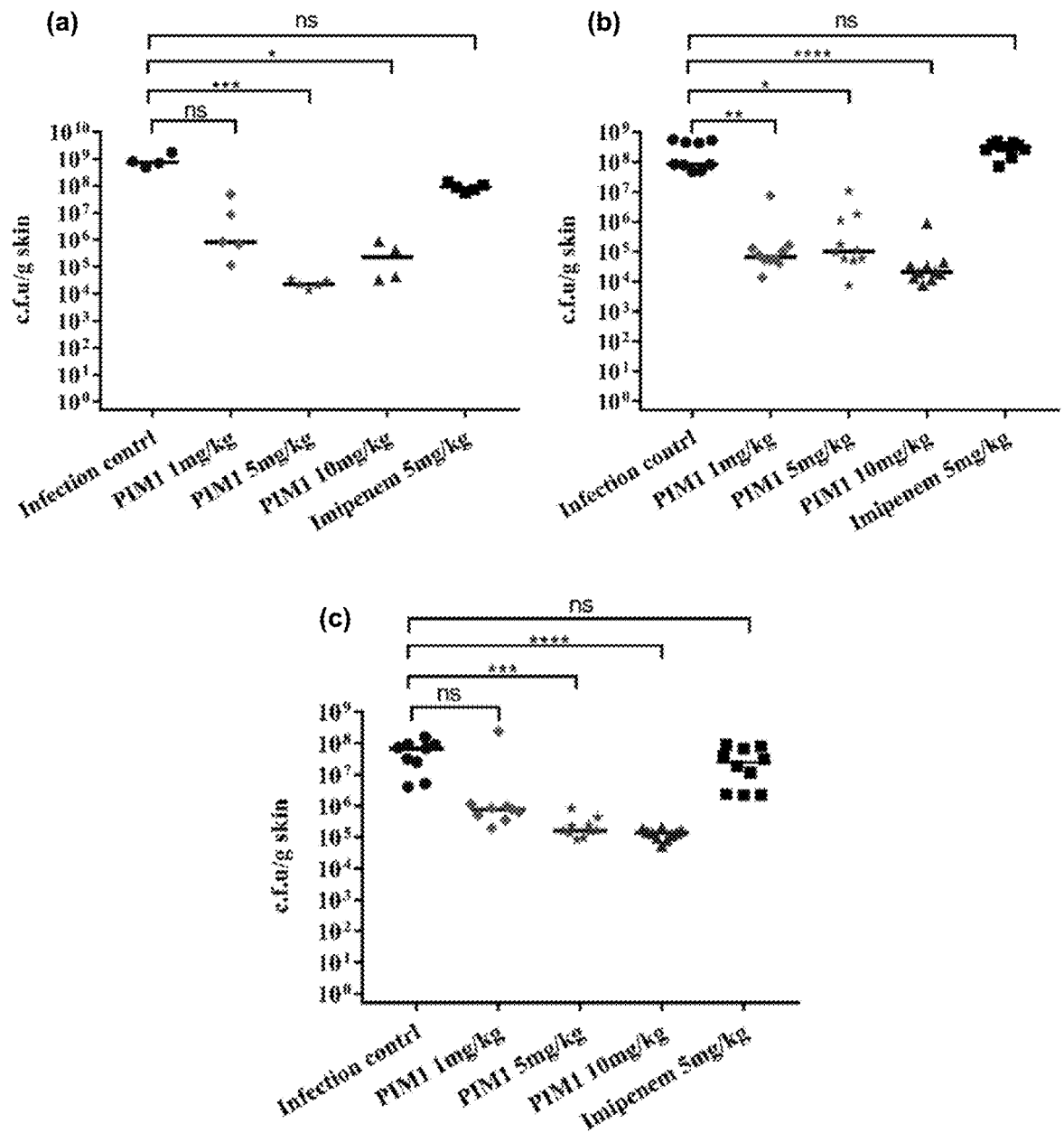
FIG. 15 Depicts the bacteria colony (CFU) on the wound of mice in a mouse skin infection model infected with (a) PAO1; (b) PAER; and (c) AB-1, with various dosage treatments. PIM 1 chloride was administered to the infected wound once at 1 mg/kg, 5 mg/kg and 10 mg/kg respectively 4 h post-infection. The control antibiotic used was 5 mg/kg of imipenem administered once at 4 h post-infection.

PIM 1 chloride was again highly active at low dose in eradicating the bacteria. When PIM 1 chloride was administered once at 1 mg/kg directly on the wound, the bacterial load was reduced by approximately 99.9% (FIG. 15b and FIG. 15c). Higher doses were well-tolerated and gave a strong antibacterial efficacy against both CRPA and CRAB bacteria.

These results demonstrate that a synthetic polymer can be effective (i.e. potent) against two of the top critical MDR gram-negative bacteria (CRAB and CAPA) both in septicemic protection and topical wound murine model, indicating that the compound is likely to be effective in a clinical setting.

Example 14. Synthesis and Properties of Acetate-Containing PIM 1-7 and Copolymers The procedure for the synthesis of the acetate-containing PIM 1-7 follows that of example 1, except that acetic acid was used instead of hydrochloric acid the same equivalent. The choice of acids used in the reaction determines the counter anions of the polyimidazoliums.

Figure 16:
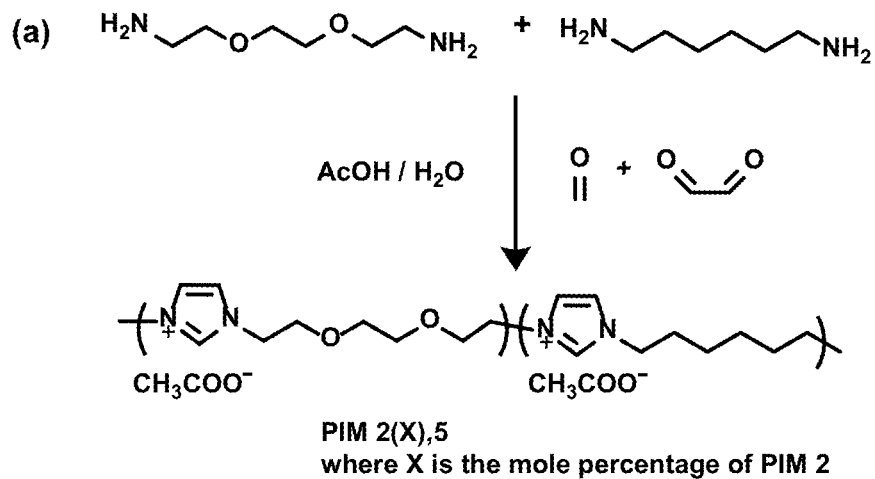
FIG. 16 Depicts the synthesis of PIM copolymers using two different diamines.
Figure 16:
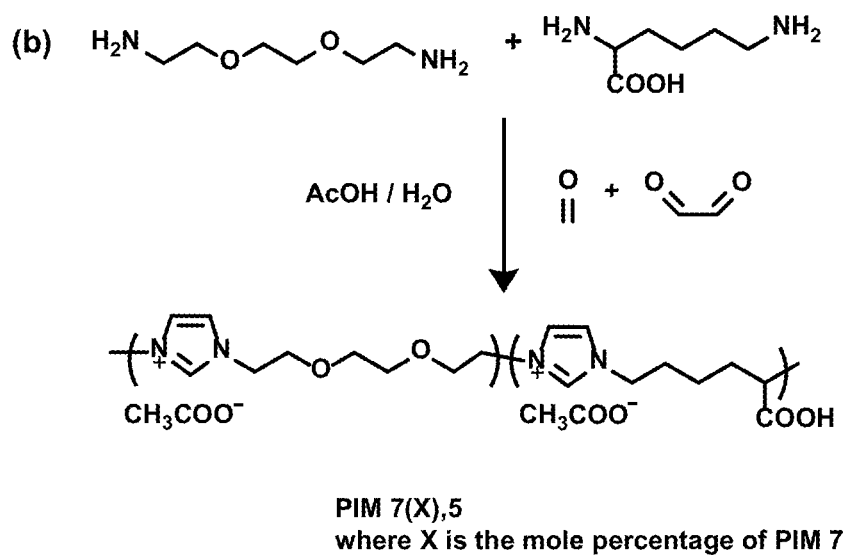

For the synthesis of acetate-containing copolymers, the procedure is similar to that of example 1, except that a mixture of two diamines in a specific mole percentage was used instead of a single type of diamine (FIG. 16). Acetic acid was used to give acetate-containing copolymers.

The acetate-containing PIM 1-7 and copolymers were then characterised, with their bactericidal properties and toxicity evaluated on a series of bacteria and on 3T3 fibroblasts respectively (Table 9), using the protocols described hereinabove. In comparison to the chloride-containing PIM 1-7 (Tables 3-8), it is clear that the acetate-containing PIM 1-7 were less effective in killing bacteria and they exhibited higher toxicity towards mammalian cells.

TABLE 9

Physical and biological properties of acetate-containing PIMs.

| Sample | GPC data summary | | | MIC$_{90}$ (μg/ml) | | | | Cell viability (%) | |
|---|---|---|---|---|---|---|---|---|---|
| | M$_n$ (×10$^3$) | M$_w$ (×10$^3$) | PDI | PAO1 | EC8739 | SA29213 | MRSA BAA40 | 100 μg/ml | 200 μg/ml |
| PIM1 | 3.2 | 6.5 | 2.03 | 8 | 16 | 8 | 8 | 5.67 | 5.40 |
| PIM2 | 4.4 | 7.1 | 1.62 | 4 | 8 | 4 | 4 | 4.67 | 5.86 |
| PIM3 | 5.8 | 11.1 | 1.91 | 32 | 32 | 32 | 32 | 7.47 | 5.11 |
| PIM4 | 27.1 | 56.4 | 2.08 | 8 | 16 | 8 | 8 | 5.91 | 5.34 |
| PIM4-2 | 2.4 | 5.8 | 2.42 | 8 | 16 | 4 | 4 | 10.31 | 9.28 |
| PIM5 | 8.0 | 17.8 | 2.22 | 8 | 16 | 16 | 16 | 22.12 | 13.61 |
| PIM2(10), 5 | 12.9 | 31.7 | 2.46 | 8 | 32 | 16 | 16 | 22.10 | 19.39 |
| PIM2(20), 5 | 10.5 | 25.3 | 2.41 | 16 | 16 | 16 | 8 | 16.76 | 14.96 |
| PIM2(40), 5 | 7.8 | 19.4 | 2.49 | 8 | 16 | 16 | 16 | 11.98 | 11.57 |
| PIM7(10), 5 | 11.9 | 33.1 | 2.78 | 8 | 16 | 32 | 16 | 14.15 | 13.04 |
| PIM7(20), 5 | 10.4 | 26.5 | 2.55 | 8 | 16 | 32 | 16 | 26.43 | 17.36 |
| PIM7(40), 5 | 9.7 | 23.0 | 2.37 | 128 | 32 | >512 | 512 | 41.71 | 34.15 |
| PIM6 | 5.9 | 18.5 | 3.14 | 8 | 32 | >512 | >512 | 62.85 | 51.31 |
| PIM7 | 11.4 | 23.3 | 2.04 | >512 | >512 | >512 | >512 | 89.70 | 78.84 |

The invention claimed is:

1. A polymer having a repeating unit of formula (I):

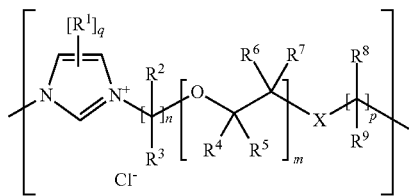

or a copolymer comprising the repeating unit of formula I and a repeating unit of formula (II):

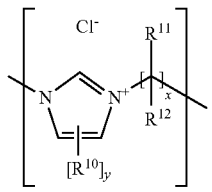

wherein:
$R^1$ and $R^{10}$, when present, independently represent $C_{1-6}$ alkyl;
each $R^2$ to $R^8$ and $R^{11}$ independently represent H or $C_{1-6}$ alkyl;
each $R^9$ and $R^{12}$ independently represents H, $C_{1-6}$ alkyl or $CO_2R^{13}$;
$R^{13}$ represents H or $C_{1-6}$ alkyl;
X represents $CR^{14}R^{15}$, O or S;
$R^{14}$ and $R^{15}$ independently represent H, $C_{1-6}$ alkyl or $CO_2R^{13}$;

the polymer comprises a —NH$_2$ or —N=CH$_2$ group as a chain terminating group; and
solvates thereof,
provided that, when the compound is a copolymer, the repeating unit of formula (I) and the repeating unit of formula (II) are not the same.

2. The polymer or copolymer according to claim 1, wherein:
$R^1$ and $R^{10}$, when present, independently represent $C_{1-3}$ alkyl;
each $R^2$ to $R^8$ and $R^{11}$ independently represents H or methyl;
each $R^9$ and $R^{12}$ independently represents H, $C_{1-3}$ alkyl or $CO_2R^{13}$;
$R^{13}$ represents H or $C_{1-3}$ alkyl;
X represents $CR^{14}R^{15}$ or O;
$R^{14}$ and $R^{15}$ independently represent H, $C_{1-3}$ alkyl or $CO_2R^{13}$;
m is a number selected from 0 to 4;
n is a number selected from 2 to 8;
p is a number selected from 1 to 3;
q is a number selected from 0 to 1;
x is a number selected from 2 to 8; and
y is a number selected from 0 to 1.

3. The polymer or copolymer according to claim 1, wherein:
each $R^2$ to $R^8$ and $R^{11}$ independently represents H;
each $R^9$ and $R^{12}$ independently represents H, methyl or $CO_2H$;
X represents $CR^{14}R^{15}$ or O;
$R^{14}$ and $R^{15}$ independently represent H, methyl or $CO_2H$;
m is a number selected from 0 to 3;
n is a number selected from 2 to 7;
p is a number selected from 1 to 2;
q and y are 0; and
x is a number selected from 2 to 7.

4. The polymer or copolymer according to claim 1, wherein:
each $R^2$ to $R^8$ and $R^{11}$ independently represents H;
each $R^9$ and $R^{12}$ independently represents H, methyl or $CO_2H$;
X represents $CR^{14}R^{15}$ or O;
$R^{14}$ and $R^{15}$ independently represent H, methyl or $CO_2H$;
m is a number selected from 0 to 2;
n is a number selected from 2 to 7;
p is a number selected from 1 to 2;
q and y are 0; and
x is a number selected from 2 to 7.

5. The polymer or copolymer according to claim 1, wherein the number average molecular weight is from 500 to 7,000 Daltons.

6. The polymer or copolymer according to claim 1, wherein the polymer or copolymer is a polymer having the repeating unit of formula I.

7. The polymer of claim 6, wherein:
each of $R^2$ to $R^8$ are H;
each $R^9$ represents H, methyl or $CO_2H$;
X represents $CH_2$ or O;
m is a number selected from 0 to 2;
n is a number selected from 2 to 6;
p is a number selected from 1 to 2; and
q is 0.

8. The polymer or copolymer according to claim 1, wherein when X is O, p is 1 or 2.

9. The polymer according to claim 1, wherein the repeating unit is selected from the group consisting of:

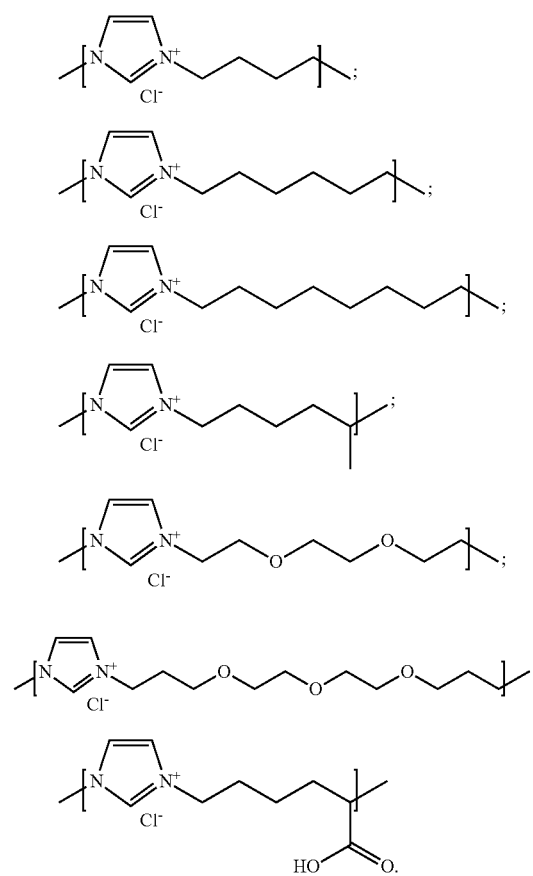

10. The copolymer according to claim 1, wherein the repeating unit of formula (I) and formula (II) are selected from the group consisting of:

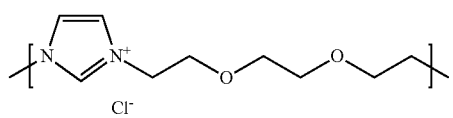

as the repeating unit of formula (I) and

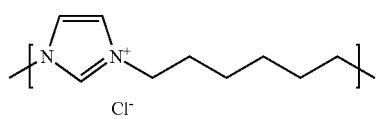

as the repeating unit of formula (II); and
(ii)

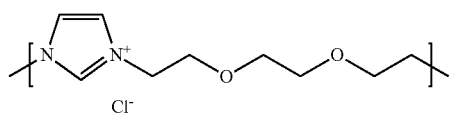

as the repeating unit of formula (I) and

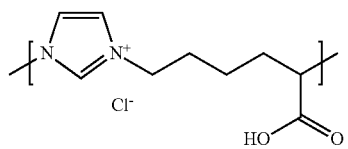

as the repeating unit of formula (II).

11. The polymer or copolymer according to claim 1 selected from the group consisting of:
(i) a polymer having the repeating unit,

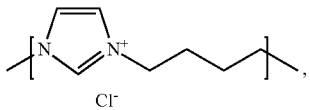

wherein the number average molecular weight of the polymer is from 500 to 2,500 Daltons;
(ii) a polymer having the repeating unit,

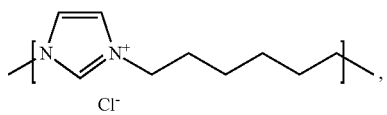

wherein the number average molecular weight of the polymer is from 500 to 2,500 Daltons;

(iii) a polymer having the repeating unit,

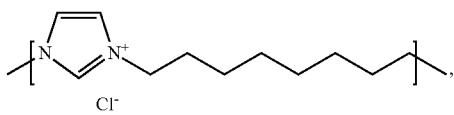

wherein the number average molecular weight of the polymer is from 500 to 2,500 Daltons;

(iv) a polymer having the repeating unit,

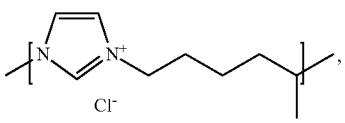

wherein the number average molecular weight of the polymer is from 500 to 2,000 Daltons;

(v) a polymer having the repeating unit,

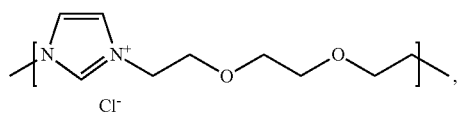

wherein the number average molecular weight of the polymer is from 4,000 to 5,500 Daltons;

(vi) a polymer having the repeating unit,

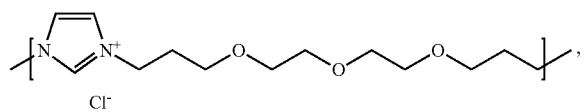

wherein the number average molecular weight of the polymer is from 4,000 to 5,000 Daltons;

(vii) a polymer having the repeating unit,

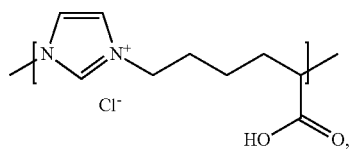

wherein the number average molecular weight of the polymer is from 500 to 2,000 Daltons;

(viii) a copolymer where the repeating unit of formula (I) and formula (II) are:

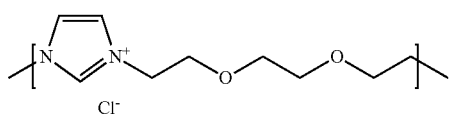

as the repeating unit of formula (I) and

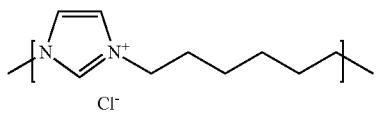

as the repeating unit of formula (II), wherein the number average molecular weight of the copolymer is from 1,000 to 5,000 Daltons; and (ix) a copolymer where the repeating unit of formula (I) and formula (II) are:

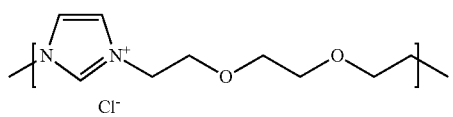

as the repeating unit of formula (I) and

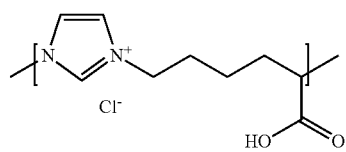

as the repeating unit of formula (II), wherein the number average molecular weight of the copolymer is from 1,000 to 5,000 Daltons.

12. The polymer according to claim 1, wherein the repeating unit is:

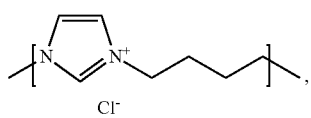

wherein the number average molecular weight of the polymer is from 500 to 2,500 Daltons.

13. The polymer or copolymer according to claim 1, wherein the number average molecular weight is from 500 to 2,500 Daltons.

14. The polymer or copolymer according to claim 1, wherein the number average molecular weight is from 500 to 2,000 Daltons.

15. The polymer according to claim 1, wherein the repeating unit is:

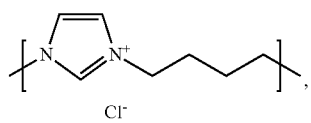

wherein the number average molecular weight of the polymer is from 500 to 2,000 Daltons.

16. A pharmaceutical composition comprising the polymer or copolymer of claim 1 and a pharmaceutically acceptable carrier.

17. An antimicrobial and/or an antifungal detergent composition comprising:
a polymer or copolymer as described in claim 1; and
a surfactant.

18. The antimicrobial and/or the antifungal detergent composition according to claim 17, wherein the composition is in the form of a solid or liquid soap.

19. The antimicrobial and/or the antifungal detergent composition according to claim 17, wherein the composition is in the form of a shampoo.

20. A method of treating a subject suffering from a microbial and/or a fungal infection comprising the step of administering to the subject a therapeutically effective amount of the polymer or copolymer of claim 1, or a pharmaceutical composition as described in claim 11, such that the infection is treated.

* * * * *